United States Patent

Ishii et al.

[11] Patent Number: 5,817,020
[45] Date of Patent: Oct. 6, 1998

[54] APPARATUS AND METHOD FOR DIAGNOSING OSTEOPOROSIS

[75] Inventors: Tetsuya Ishii; Masashi Kuriwaki; Yasuyuki Kubota, all of Kyoto, Japan

[73] Assignee: Sekisui Kagaku Kogyo Kabushiki Kaisya, Osaka, Japan

[21] Appl. No.: 875,354

[22] PCT Filed: Nov. 28, 1996

[86] PCT No.: PCT/JP96/03489

§ 371 Date: Jul. 29, 1997

§ 102(e) Date: Jul. 29, 1997

[87] PCT Pub. No.: WO97/19641

PCT Pub. Date: Jun. 5, 1997

[30] Foreign Application Priority Data

| | | | |
|---|---|---|---|
| Nov. 29, 1995 | [JP] | Japan | 7-311340 |
| Nov. 29, 1995 | [JP] | Japan | 7-311341 |
| Feb. 20, 1996 | [JP] | Japan | 8-031967 |
| Mar. 26, 1996 | [JP] | Japan | 8-069840 |

[51] Int. Cl.$^6$ ............................. A61B 8/00
[52] U.S. Cl. ............................. 600/437
[58] Field of Search ............... 600/449, 444, 600/437; 73/59

[56] References Cited

U.S. PATENT DOCUMENTS 4,930,511  6/1990  Rossman et al.

FOREIGN PATENT DOCUMENTS

| | | |
|---|---|---|
| 61-180007 | 11/1986 | Japan. |
| 4-54944 | 2/1992 | Japan. |
| 5-237108 | 9/1993 | Japan. |
| 8-25196 | 8/1996 | Japan. |
| 8-332186 | 12/1996 | Japan. |

Primary Examiner—Marvin M. Lateef
Assistant Examiner—Maulin Patel
Attorney, Agent, or Firm—Oblon, Spivak, McClelland, Maier & Neustadt, P.C.

[57] ABSTRACT

The apparatus for diagnosing osteoporosis in the present invention radiates repeated ultrasonic pulses $A_i$ toward cortical bone Mb in a subject and receives echoes Ae from the bone Mb. The received signal is converted to a digital echo signal by an A/D converter 8, and the echo level is detected by a CPU 11. The CPU 11 extracts the maximum echo level from the echo levels detected during the measurement period and calculates the acoustic impedance Zb of the cortical bone based on the maximum echo level which has been extracted. The bone density of the subject is calculated from the detected acoustic impedance Zb of the cortical bone using a predetermined recurrence formula. The acoustic impedance of bone is given by the square root of [the elastic modulus×density] of bone, and since the elastic modulus of bone increases (or decreases) as bone density increases (or decreases), the elastic modulus of bone and bone density play a synergistic role in the acoustic impedance. The acoustic impedance Zb of bone is thus a good index for assessing bone density.

45 Claims, 14 Drawing Sheets

——— WAVEFRONT (CREST) OF ECHO Ae
·········· WAVEFRONT (TROUGH) OF ECHO Ae
——— WAVEFRONT (CREST) OF EMITTED SUPERSONIC PULSE
·········· WAVEFRONT (TROUGH) OF EMITTED SUPERSONIC PULSE

APPARATUS AND METHOD FOR DIAGNOSING OSTEOPOROSIS

DESCRIPTION

1. TECHNICAL FIELD

This invention relates to an ultrasonic reflection type of apparatus and method for diagnosing osteoporosis by emitting ultrasonic pulses toward predetermined cortical bone in a subject so as to measure the echo levels from the surface of the cortical bone.

2. BACKGROUND ART

With the advent of an ageing society in recent years, the bone disease referred to as osteoporosis has become a problem. This is a disease in which the loss of bone calcium results in brittleness and susceptibility to fractures with minimal trauma, and can cause the elderly to become bedridden. The physical diagnosis of osteoporosis is managed by the precise measurement of bone density using a diagnostic apparatus featuring the use of X-rays such as DXA, but problems involved in physical diagnosis with X-rays are that the equipment is large and expensive, and its use is limited in many ways in the interests of protecting against harm caused by radiation exposure.

Diagnostic apparatuses featuring the use of transmitted ultrasonic waves or reflected ultrasonic waves have begun to enjoy more popularity as simple devices which do not suffer from such drawbacks.

The diagnostic apparatuses noted in Japanese Laid-Open Patent Application 2-104337 and U.S. patent application Ser. No. 193,295 are known as ultrasonic transmitting types of diagnostic devices. In these diagnostic apparatuses, the acoustic velocity in bone is measured by setting up two ultrasonic transducers facing each other on either side of a part of a subject's body, so that ultrasonic pulses are emitted from one ultrasonic transducer at the osseous tissue, and the ultrasonic pulses passing through the osseous tissue are received by the other ultrasonic transducer. The extent of osteoporosis is diagnosed on the assumption that a slower acoustic velocity in osseous tissue indicates lower bone density due to loss of bone calcium.

The theoretical basis linking bone density and acoustic velocity is uncertain, however. Strictly speaking, the acoustic velocity in osseous tissue is not proportional to bone density, but is given by the square root of [the elastic modulus of bone/bone density]. Furthermore, because the elastic modulus of bone and bone density play mutually cancelling roles in acoustic velocity, where increases in the bone density (denominator) are met by increases in the elastic modulus of bone (numerator), the acoustic velocity in osseous tissue is not capable of sensitive response to increases in bone density. As such, there is not that high a correlation between the acoustic velocity in osseous tissue and bone density. Reliability is accordingly a problem in conventional ultrasonic transmission types of diagnostic apparatuses in which bone density is estimated on the basis of the acoustic velocity in osseous tissue.

Ultrasonic reflection types of diagnostic apparatuses have meanwhile been proposed by the applicant in Japanese Patent Applications 6-310445, 7-140730, 7-140731, 7-140732, 7-140733, and 7-140734, and International Laid-Open Patent Application WO 96/18342. In these diagnostic apparatuses, a single ultrasonic transducer capable of both transmission and reception is used to emit ultrasonic pulses toward cortical bone in a subject, echoes reflected on the surface of the cortical bone are received, and the acoustic impedance of the subject's cortical bone is calculated on the basis of the resulting echo data. The progress of osteoporosis is then diagnosed based on the level of the acoustic impedance thus calculated.

The acoustic impedance of bone is given by the square root of [the elastic modulus×density] of bone, and since, as described above, the elastic modulus of bone increases (or decreases) as bone density increases (or decreases), the elastic modulus of bone and bone density play a synergistic role in acoustic impedance. Thus, the latter ultrasonic reflection type of apparatus in which acoustic impedance is used as an index can be considered more reliable because it is capable of more sensitive response to the extent of the progress of osteoporosis than is the former ultrasonic transmission type of apparatus in which acoustic velocity is used as an index.

Although acoustic impedance can be considered a sensitive indicator of the progress of osteoporosis, in the final analysis it is only an index of bone density, which does not mean that the bone density itself is determined. Furthermore, when the acoustic impedance of cortical bone is lower than that of soft tissue, or when the cortical bone is thinner than the ultrasonic wavelength, there is a problem in that the acoustic impedance of cortical bone cannot be measured or that such measurement is uncertain.

In view of the foregoing, a first object of the present invention is to provide an ultrasonic reflection type of apparatus and method for diagnosing osteoporosis, which is simple, with no danger of exposure to radiation, yet is capable of determining bone density. A second object of the present invention is to provide an ultrasonic reflection type of apparatus and method for diagnosing osteoporosis, which is capable of highly reliable diagnosis, even when the acoustic impedance of the cortical bone is lower than that of the soft tissue and when the cortical bone is thinner than the ultrasonic wavelength.

SUMMARY OF THE INVENTION

In the apparatus (and method) for diagnosing osteoporosis in the present invention, ultrasonic pulses are repeatedly emitted toward cortical bone in a subject, the echoes reflected on the surface of the cortical bone at that time are received, and osteoporosis is diagnosed based on the resulting echo data.

As such, a first aspect of the present invention is to provide an apparatus for diagnosing osteoporosis, comprising: an echo level detecting means for detecting the echo level of the echoes reflected on the surface of the cortical bone when the ultrasonic pulses are emitted; a maximum echo level extracting means for extracting the maximum echo level from among the echo levels thus detected; a reflection coefficient calculating means for calculating the ultrasonic reflection coefficient at the interface between the soft tissue and cortical bone of the subject based on the maximum echo level that has been extracted; and a bone density calculating means for calculating the density of the subject's cortical bone using a predetermined recurrence formula for the cortical bone density relative to the ultrasonic reflection coefficient.

In a preferred embodiment of the bone density calculating means, the recurrence formula for the cortical bone density relative to the ultrasonic reflection coefficient is given in the form of Formula (1) or (2)

$$\rho = \alpha' R + \beta' \tag{1}$$

ρ: density of cortical bone [kg/m³]
R: ultrasonic reflection coefficient at interface between soft tissue and cortical bone of subject
α': regression coefficient [kg/m³]
β': section [kg/m³]

The regression coefficient α' should be established within the range of 588 to 1100, and the section β' should be established within the range of 953 to 1060.

$$\rho = B'R^{A'} \quad (2)$$

A': regression coefficient
B': constant [sec/m]

A second aspect of the present invention is to provide an apparatus, comprising: an echo level detecting means for detecting the echo level of the echoes reflected on the surface of the cortical bone when the ultrasonic pulses are emitted; a maximum echo level extracting means for extracting the maximum echo level from among the echo levels thus detected; an acoustic impedance calculating means for calculating the acoustic impedance of the subject's cortical bone based on the maximum echo level that has been extracted; and a bone density calculating means for calculating the density of the subject's cortical bone using a predetermined recurrence formula for the cortical bone density relative to the acoustic impedance.

In a preferred embodiment of the bone density calculating means, the recurrence formula for cortical bone density relative to acoustic impedance is given by Formula (3) or (4).

$$\rho = \alpha Zb + \beta \quad (3)$$

ρ: density of cortical bone [kg/m³]
Zb: acoustic impedance of cortical bone in subject [kg/m²sec]
α: regression coefficient [sec/m]
β: section [kg/m³]

The regression coefficient α should be established within the range of $1.27 \times 10^{-4}$ to $2.34 \times 10^{-4}$, and the section β should be established within the range of 646 to 887.

$$\rho = BZb^{A} \quad (4)$$

A: regression coefficient
B: constant [sec/m]

The regression coefficient A should be established with the range of 0.239 to 0.445, and the constant B should be established within the range of $10^{0.239}$ to $10^{1.55}$.

A third aspect of the present invention is to provide an apparatus for diagnosing osteoporosis, comprising: an echo waveform detecting means for detecting the reception waveform of the echoes reflected on the surface of the cortical bone when the ultrasonic pulses are emitted; a maximum echo waveform extracting means for extracting the maximum echo reception waveform by comparing the plurality of echo reception waveforms that have been detected; a Fourier transform treatment means for finding the maximum echo spectrum by the Fourier transform treatment of the maximum echo reception waveform; and a complex reflection coefficient calculating means for calculating the ultrasonic complex reflection coefficient (complex acoustic characteristics data) of cortical bone relative to the soft tissue of the subject based on the maximum echo spectrum thus determined, wherein osteoporosis is diagnosed on the basis of the ultrasonic complex reflection coefficient thus calculated.

A preferred embodiment of the third aspect further comprises a diagnostic means for obtaining amplitude data and phase data from the ultrasonic complex reflection coefficient thus calculated, and for diagnosing osteoporosis based on the resulting amplitude and phase data.

A fourth aspect of the present invention is to provide an apparatus for diagnosing osteoporosis, comprising: an echo waveform detecting means for detecting the reception waveform of the echoes reflected on the surface of the cortical bone when the ultrasonic pulses are emitted; a maximum echo waveform extracting means for extracting the maximum echo reception waveform by comparing the plurality of echo reception waveforms that have been detected; a Fourier transform treatment means for finding the maximum echo spectrum by the Fourier transform treatment of the maximum echo reception waveform; and a complex acoustic impedance calculating means for calculating the complex acoustic impedance (complex acoustic characteristics data) of the subject's cortical bone based on the maximum echo spectrum thus determined, wherein osteoporosis is diagnosed on the basis of the complex acoustic impedance thus calculated.

A preferred embodiment of the fourth aspect further comprises a diagnostic means for obtaining amplitude data and phase data from the complex acoustic impedance thus calculated, and for diagnosing osteoporosis based on the resulting amplitude and phase data.

A fifth aspect of the present invention is to provide a method for diagnosing osteoporosis, wherein an ultrasonic transducer is placed on a predetermined area on the surface of a subject's skin, ultrasonic pulses are repeatedly emitted toward cortical bone below the skin, the echoes reflected on the surface of the cortical bone at that time are received so as to detect the echo level, the maximum echo level is extracted from the echo levels thus detected, the ultrasonic reflection coefficient at the interface between the soft tissue and the cortical bone of the subject is calculated based on said extracted maximum echo level, and the density of the subject's cortical bone is then calculated using a predetermined recurrence formula for the cortical bone density relative to the ultrasonic reflection coefficient.

A sixth aspect of the present invention is to provide a method for diagnosing osteoporosis, wherein an ultrasonic transducer is placed on a predetermined area on the surface of a subject's skin, ultrasonic pulses are repeatedly emitted toward cortical bone below the skin, the echoes reflected on the surface of the cortical bone at that time are received so as to detect the echo level, the maximum echo level is extracted from the echo levels thus detected, the acoustic impedance of the cortical bone of the subject is calculated based on said extracted maximum echo level, and the density of the subject's cortical bone is then calculated using a predetermined recurrence formula for the cortical bone density relative to the acoustic impedance.

A seventh aspect of the present invention is to provide a method for diagnosing osteoporosis, wherein an ultrasonic transducer is placed on a predetermined area on the surface of a subject's skin, ultrasonic pulses are repeatedly emitted toward cortical bone below the skin, the reception waveforms of the echoes reflected on the surface of the cortical bone at that time are received so as to detect the echo reception waveforms, the maximum echo is extracted from the echo reception waveforms thus detected, the maximum echo spectrum is determined by the Fourier transform treatment of the maximum echo reception waveform, the ultrasonic complex reflection coefficient of the cortical bone relative to the soft tissue of the subject is calculated based on the maximum echo spectrum that has been determined, and osteoporosis is diagnosed based on the amplitude data and phase data obtained from the ultrasonic complex reflection coefficient thus calculated.

An eighth aspect of the present invention is to provide a method for diagnosing osteoporosis, wherein an ultrasonic transducer is placed on a predetermined area on the surface of a subject's skin, ultrasonic pulses are repeatedly emitted toward cortical bone below the skin, the reception waveforms of the echoes reflected on the surface of the cortical bone at that time are received so as to detect the echo reception waveforms, the maximum echo is extracted from the echo reception waveforms thus detected, the maximum echo spectrum is determined by the Fourier transform treatment of the maximum echo reception waveform, the complex acoustic impedance of the cortical bone of the subject is calculated based on the maximum echo spectrum that has been determined, and osteoporosis is diagnosed based on the amplitude data and phase data obtained from the complex acoustic impedance thus calculated.

BEST MODE FOR CARRYING OUT THE INVENTION

The best modes for carrying out the invention are described below with reference to the drawings. The invention is described in detail using embodiments.
Embodiment 1

Figure 1:
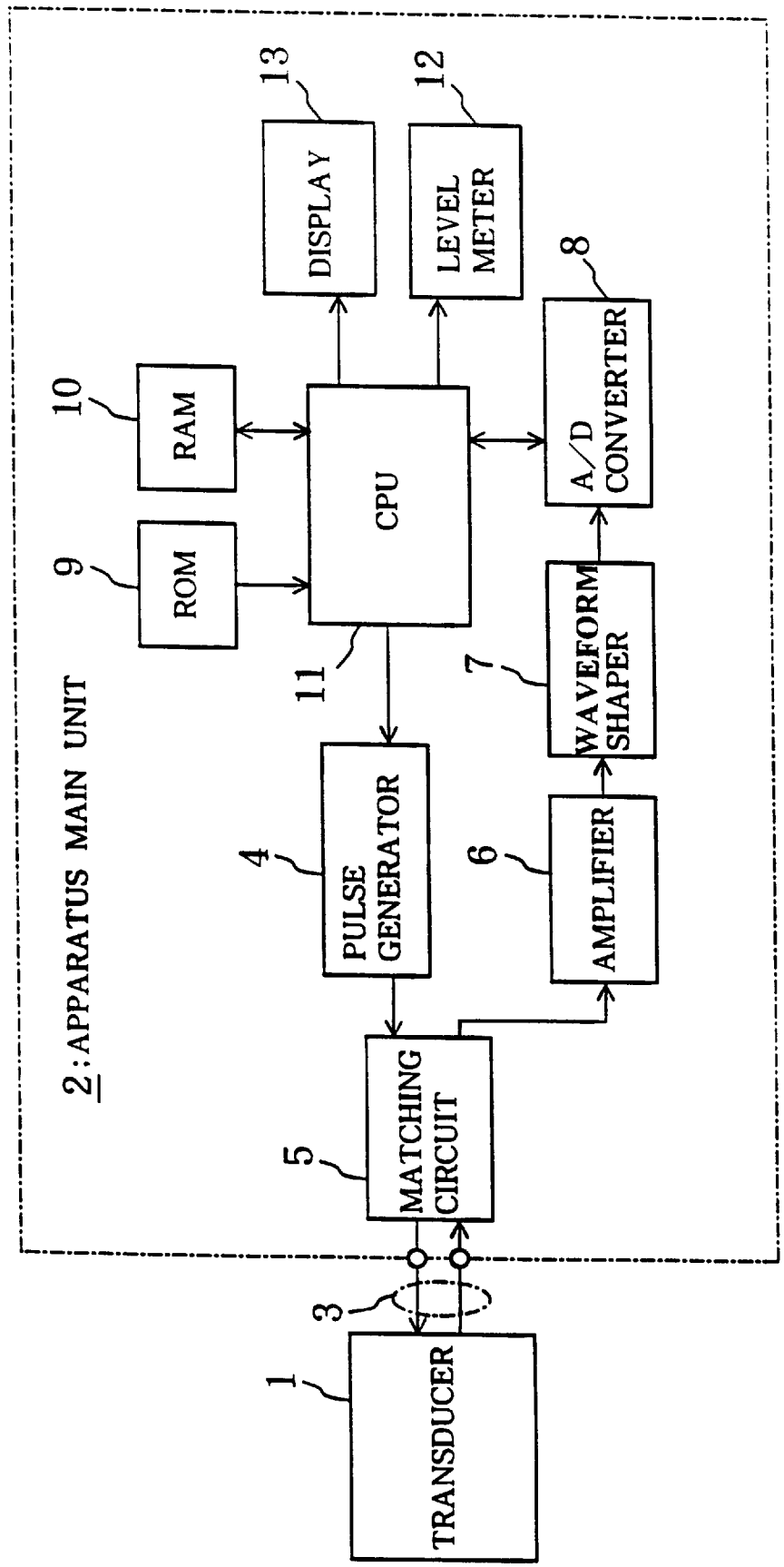
FIG. 1 is a block diagram depicting the electrical structure of the apparatus for diagnosing osteoporosis in a first embodiment of the invention.
Figure 2:
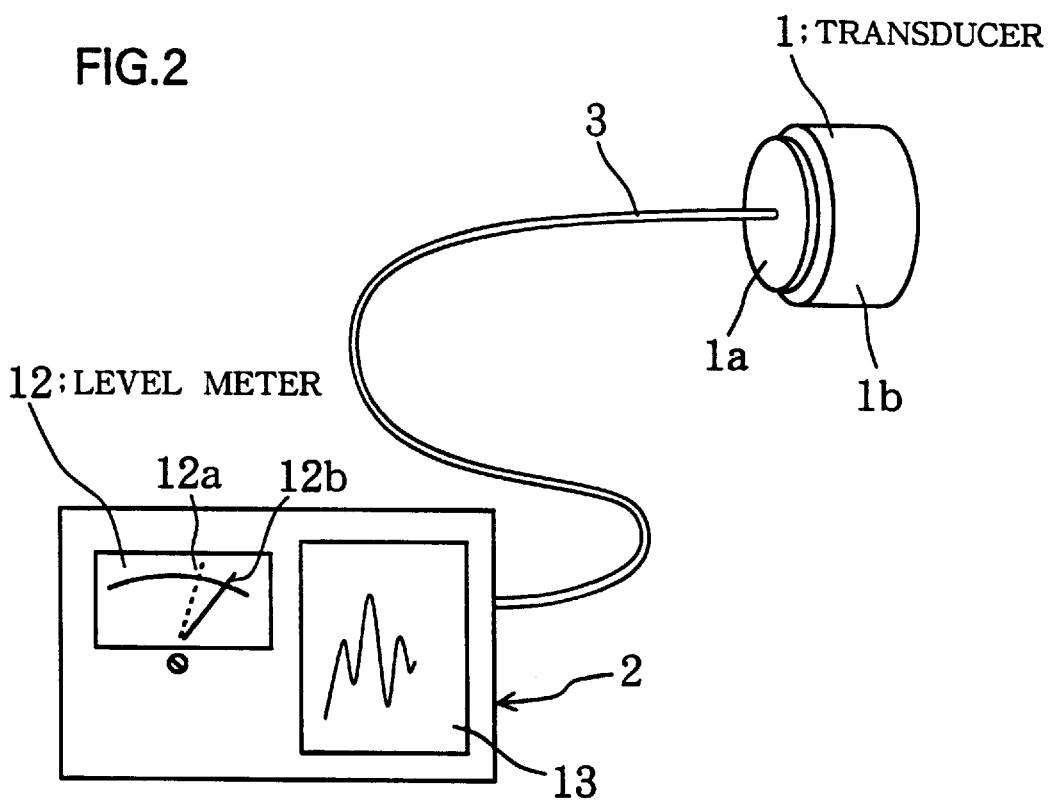
FIG. 2 is a schematic outer view of the same apparatus.
Figure 6A:
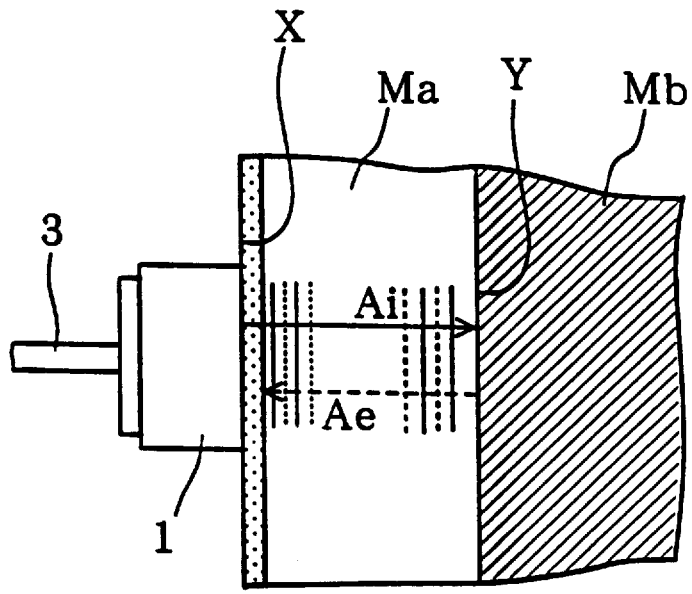
Figure 6B:
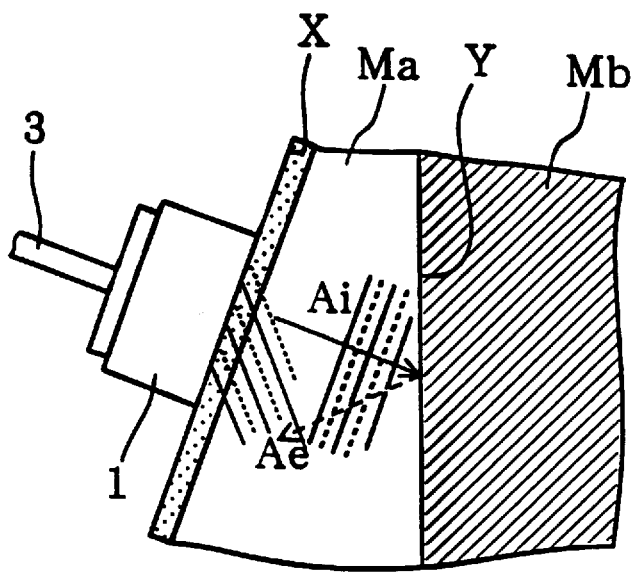
Figure 7:
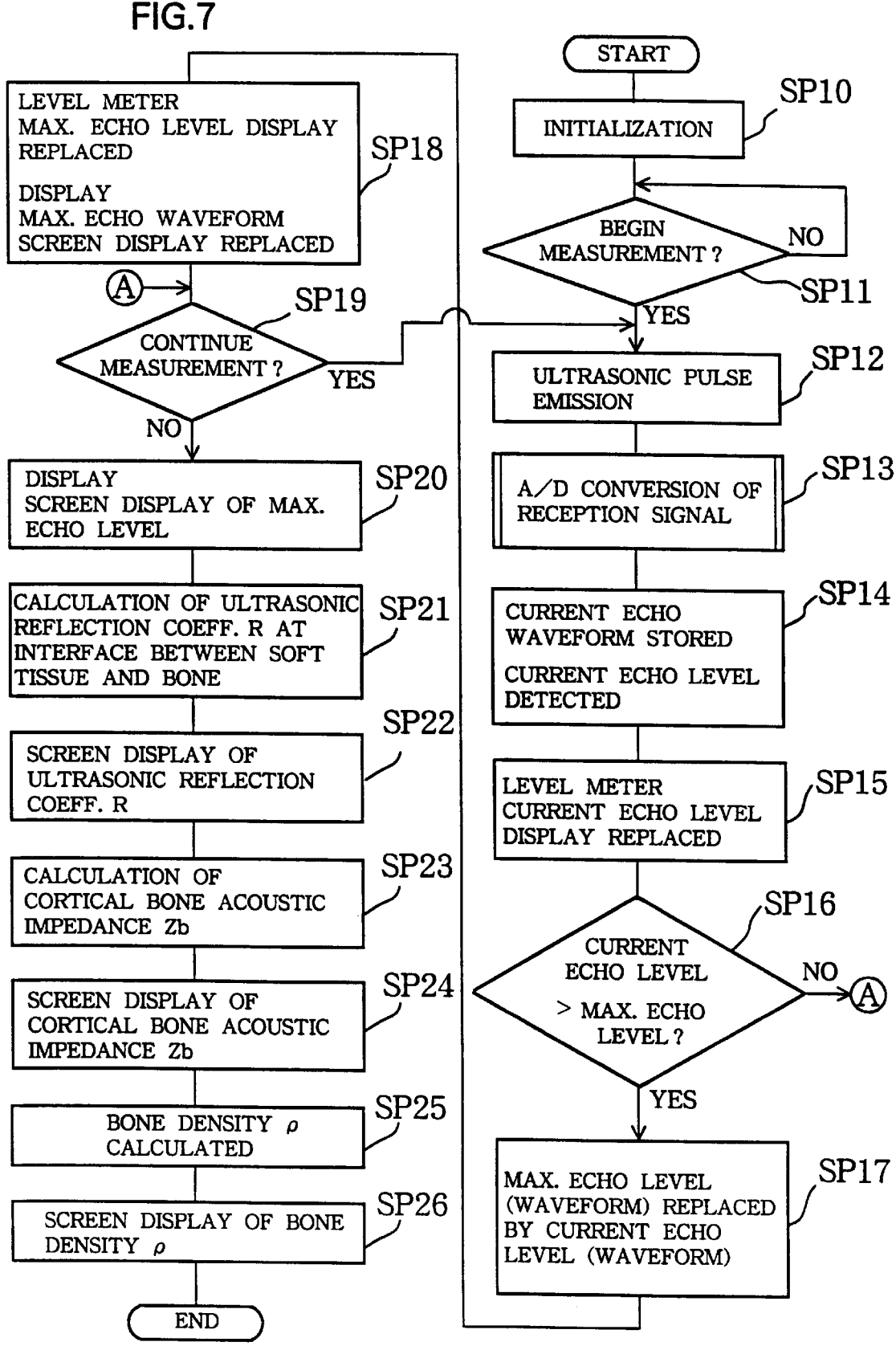
FIG. 7 is a flow chart of the operation of the same apparatus.
Figure 8:
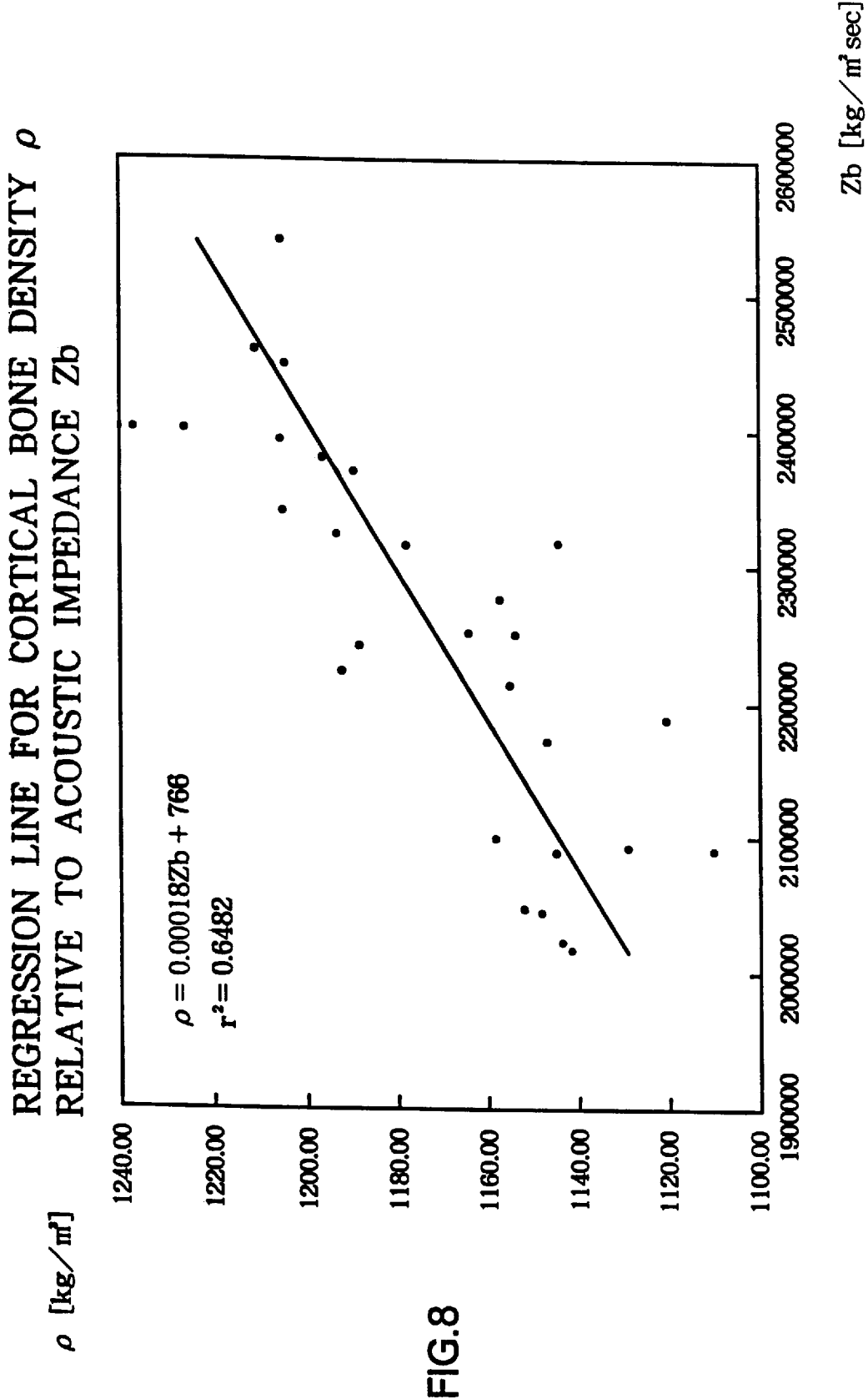
FIG. 8 is a graph of the regression line for cortical bone density $\rho$ relative to the acoustic impedance Zb, and is used to describe the contents of the bone density calculating subprogram constituting the same apparatus.

FIG. 1 is a block diagram depicting the electrical structure of the apparatus for diagnosing osteoporosis in a first embodiment of the invention; FIG. 2 is a schematic outer view of the same apparatus; FIGS. 3 through 6 are illustrations used to describe the operation of the apparatus; FIG. 7 is a flow chart of the operation of the same apparatus; FIG. 8 is a graph of the regression line for cortical bone density $\rho$ relative to the acoustic impedance Zb, and is used to describe the bone density calculating subprogram constituting the same apparatus.

As shown in FIGS. 1 and 2, the apparatus for diagnosing osteoporosis in this example comprises: an ultrasonic transducer 1 (hereinafter simply referred to as transducer), which emits ultrasonic pulses toward predetermined cortical bone in a subject at a measuring location in response to electrical pulse signals that are input at a predetermined period, and receives echoes (reflected waves) from the surface of the cortical bone and converts them to a reception signal (electrical signal); an apparatus main unit 2, which carries out the diagnosis of osteoporosis by supplying electrical pulse signals to the transducer 1 and processing the reception signals output from the transducer 1 so as to extract the echo level (reflection wave amplitude) from the cortical bone; and a cable 3 connecting the transducer 1 and apparatus main unit 2.

Figure 3:
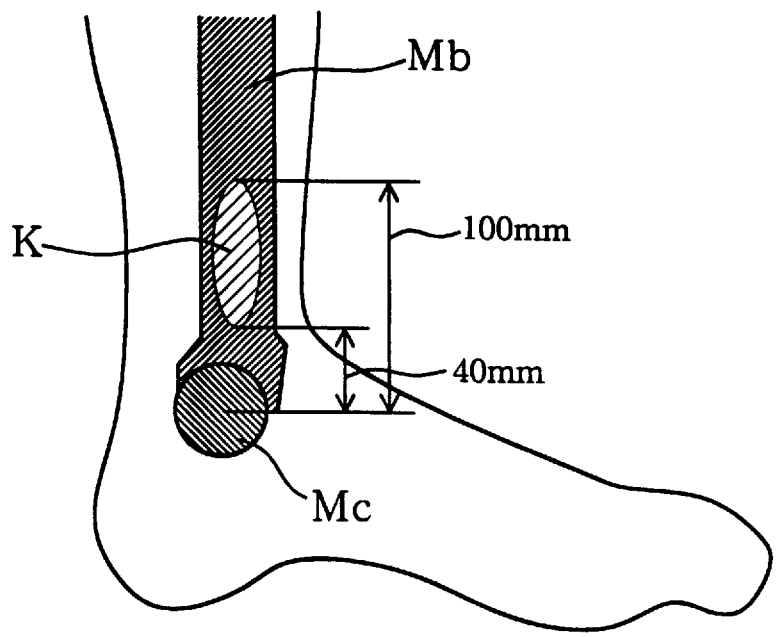
FIGS. 3 through 6 are illustrations used to describe the operation of the apparatus.

The aforementioned transducer 1 consists primarily of an ultrasonic oscillator 1a having electrode layers on either side of a disk-shaped thickness oscillation type of piezo-electric element of lead zirconate titanate (PZT) or the like. An ultrasonic delay spacer 1b of a polyethylene bulk or the like is fixed to one of the electrode surfaces (ultrasonic pulse transducer surface) of the ultrasonic oscillator 1a in order to eliminate the effects of transmission reverberation. Here, cortical bone can be irradiated with nearly flat ultrasonic pulses from the transducer surface of the transducer 1 to carry out highly accurate measurements, and nearly flat echoes should be reflected from the cortical bone to the transducer surface, so the transducer 1 is ideally constructed of a piezo-electric element with a relatively large disk radius to make the transducer surface as wide as possible (in this example, the diameter D of the transducer surface is 15 mm). From a similar perspective, the measuring site that is used should be the cortical bone of the heel, top of the patella, tibia, scapula, cranial bone, or the like, which can be regarded as being flat, with a large curvature radius, and which is close to the surface of the skin. As a result of detailed measurements at various locations of cortical bone in humans, the inventors of the present application found that an ideal measuring location was the cortical bone of the lower tibia, especially within a range K of 40 mm to 100 mm over the ankle Mc, as shown in FIG. 3, because virtually noise-free echoes alone were extracted independently from the lower tibia Mb far more frequently than with the cortical bone in other locations. When the influence of transmission reverberation is negligible, the ultrasonic delay spacer 1b can be omitted.

The aforementioned apparatus main unit 2 comprises a pulse generator 4, matching circuit 5, amplifier 6, waveform shaper 7, A/D convertor 8, ROM 9, RAM 10, CPU (central processing unit) 11, level meter 12, and display 13.

The pulse generator 4 is connected via a cable 3 to the transducer 1, and repeatedly produces an electrical pulse signal with a central frequency of, for example, 1 MHz or 2.5 MHz at a predetermined period (100 msec, for example), which is sent to the transducer 1. The matching circuit 5 matches impedance, to allow the signals to be transmitted and received at optimal energy efficiency between the transducer 1 and apparatus main unit 2 which are connected by the cable 3. Thus, when the ultrasonic oscillator 1a of the transducer 1 receives echoes from cortical bone, the reception signal is output from the transducer 1 and is input to the amplifier 6 via the matching circuit 5 with no loss of energy. The amplifier 6 amplifies the reception signal input through the matching circuit to a predetermined amplification level and then inputs it to the waveform shaper 7. The waveform shaper 7 consists of a band pass filter having an LC structure, and filters the reception signal that has been amplified by the amplifier 6 to shape the waveform to a linear form in order to eliminate noise, and the signal is then input to the A/D convertor. The A/D convertor 8 is equipped with a sample holder circuit not shown in the figure, sampling memory (SRAM), and the like, and samples the output signal from the waveform shaper 7 (waveform shaped analog reception signal) at a predetermined frequency (such as 12 MHz) when the CPU 11 sends a command to start sampling, so as to sequentially convert the signals to digital signals, and the resulting digital signals are temporarily stored in the sampling memory itself and then sent to the CPU 11.

The ROM 9 stores the operating system (OS) as well as the various processing programs of the CPU 11, specifically, the maximum echo level extracting subprogram, reflection coefficient calculating subprogram, acoustic impedance calculating subprogram, and bone density calculating subprogram.

A procedure for taking in the digital signal from the sampling memory of the A/D convertor 8 for each pulse and echo to detect the echo level for each echo, and a processing procedure for extracting the maximum echo level from the echo levels that are detected for each echo, are written to the maximum echo level extraction subprogram. A processing procedure for calculating the ultrasonic reflection coefficient R during roughly perpendicular reflection at the interface between the soft tissue and cortical bone (measuring location) of the patient based on the maximum echo level value given by the maximum echo level extraction subprogram is written to the reflection coefficient calculating subprogram. A procedure for calculating the acoustic impedance Zb using Formula (5) based on the values calculated for the ultrasonic reflection coefficient R given by the reflection coefficient calculating subprogram is written to the acoustic impedance calculating subprogram.

$$Zb = Za(R+1)/(1-R) \tag{5}$$

Za: acoustic impedance of soft tissue Formula (5) is derived from Formula (6). As shown in FIG. 6(a), the surface Y of cortical bone Mb can be regarded as being flat, and the ultrasonic pulse Ai generated from the transducer 1 can also be regarded as being flat, so when the wavefront is parallel to the surface Y of the cortical bone Mb (lands roughly perpendicular), the ultrasonic reflection coefficient is expressed by Formula (6). As will be described below, the echo level is greatest when the wavefront of a flat wave and the surface Y of cortical bone Mb are parallel. Accordingly, the ultrasonic reflection coefficient given by Formula (6) is the ultrasonic reflection coefficient when the maximum echo level is obtained. Formula (5) is thus obtained by transforming Formula (6).

$$R = (Zb-Za)/(Zb+Za) \tag{6}$$

The bone density calculating subprogram contains a processing procedure for the bone density (cortical bone density) $\rho$ of a patient using Formula (7) based on the value calculated for the acoustic impedance Zb given by the acoustic impedance calculating subprogram.

Here, Formula (7) is the recurrence formula of the bone density $\rho$ relative to the acoustic impedance Zb, which is obtained by prior examination of a specimen, as shown in FIG. 8.

$$\rho = \alpha Zb + \beta \tag{7}$$
$$= 1.80 \times 10^{-4} ZB + 766$$

$\rho$: cortical bone density [$kg/m^3$]

Zb: acoustic impedance of cortical bone [$kg/m^2 sec$]

$\alpha$: regression coefficient of bone density relative to acoustic impedance [$sec/m$]

$\beta$: section [$kg/m^3$]

In the examination of the specimen described above, the acoustic impedance Zb was measured for the cortical bone of the tibia using ultrasonic reflection, and the density $\rho$ of the cortical bone Mb was measured by X-ray (QCT) of the radius (arm bone). Examination of the specimen revealed a high correlation (r=0.67) between the acoustic impedance Zb and the bone density $\rho$ measured by X-ray (QCT). Statistical hypothesis testing resulted in a 95% probability (reliability) that a patient's bone density $\rho$ would fall within the $\rho$min to $\rho$max range when the value for the acoustic impedance Zb of the cortical bone of any patient is Zb. The significance level is thus 5%.

Here, $\rho$min is given by Formula (8), and $\rho$max is given by Formula (9).

$$\rho min = (1.80 \times 10^{-4} - 30\%) Zb + (766 - 16\%) \tag{8}$$
$$\rho max = (1.80 \times 10^{-4} + 30\%) Zb + (766 + 16\%) \tag{9}$$

RAM 10 has a working area in which the working area for the CPU 11 is established, and a data area in which various data are temporarily stored. The data area contains an echo level memory area for storing the most recently detected echo level (hereinafter referred to as current echo level) or maximum echo level, an echo waveform memory area for storing the most recently detected echo waveform (current echo waveform) or maximum echo waveform, and a measurement continue flag or the like for storing data on whether or not to continue measurement.

The CPU 11 executes the various processing programs stored in the ROM 9 using RAM 10 to start the pulse generator 4 or A/D convertor 8, controls the various components of the apparatus to detect echo levels for each pulse and echo, extracts the maximum echo level, and calculates the bone density $\rho$ of the patient based on the maximum echo level value detected, so as to diagnose osteoporosis.

The level meter 12 is controlled by the CPU 11 and displays the current echo level stored in RAM 10 by the deflection of the liquid crystal needle pattern 12a indicated by the broken line in FIG. 2 as well as the maximum echo level, which is the greatest echo level among those thus far detected, by the deflection of the liquid crystal needle patten 12b indicated by the solid line in the figure. The display 13 consists of a CRT display or liquid crystal display. The measured values of the echo levels and the like, the ultrasonic reflection coefficient R, the acoustic impedance Zb, the calculated values of the bone density $\rho$, and the echo waveforms are displayed on screen under the control of the CPU 11.

The operation of this example (course of CPU 11 processing during diagnosis of osteoporosis) is described below with reference to FIGS. 4 through 7.

Figure 4:
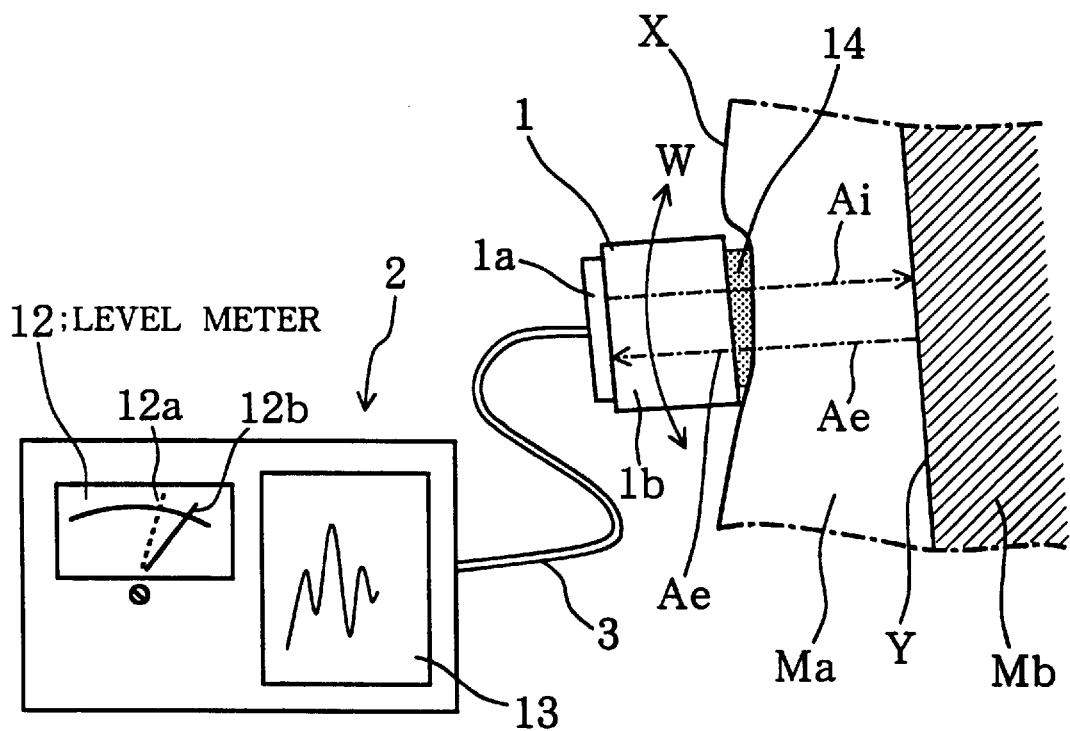
Figure 5:
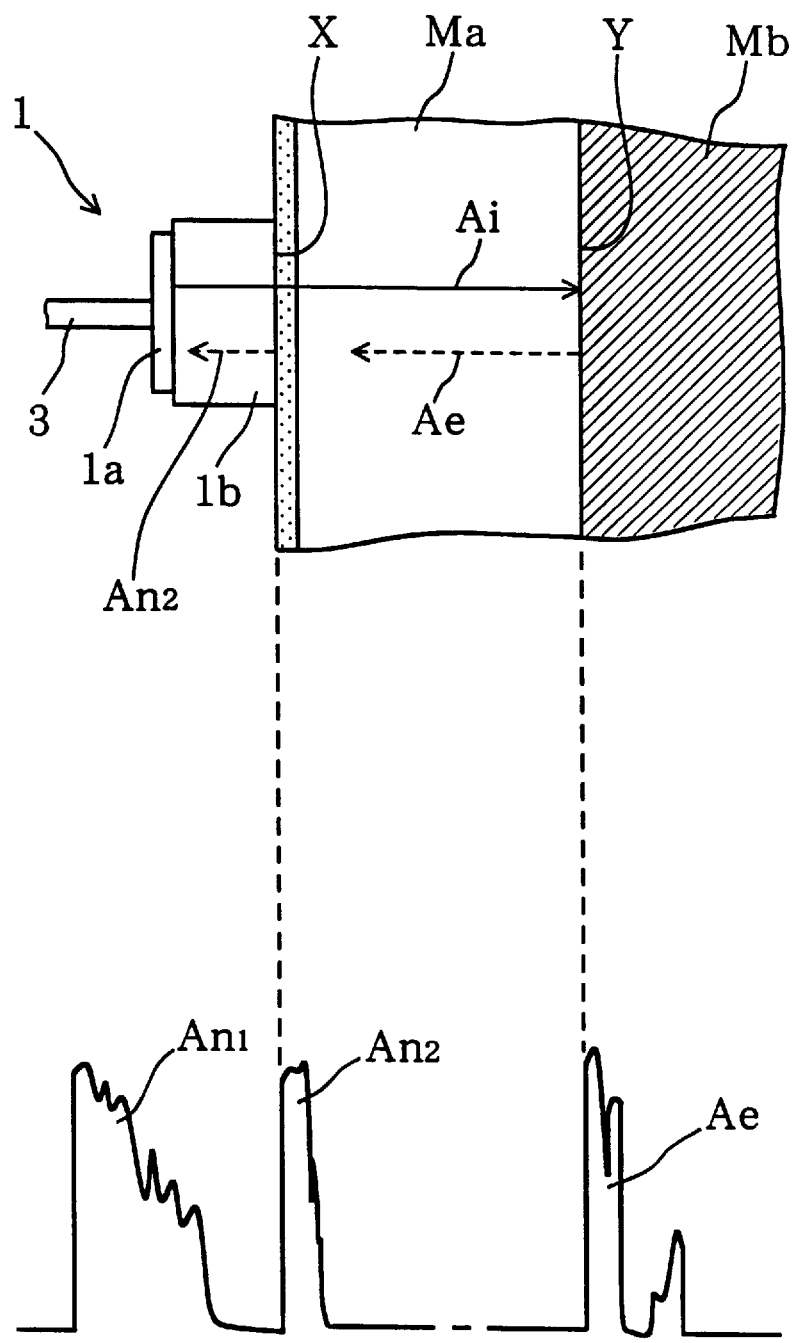

First, the cortical bone of the lower tibia, particularly within a range K of 40 mm to 100 mm above the ankle Mc, is selected. Of course, the cortical bone of other desirable locations such as the heel, top of the patella, scapula, and cranial bone may also be selected as needed. When the power source is turned on in the apparatus, the CPU 11 presets the various components of the apparatus and initializes the counter, the various registers, and the various flags, and waits for the measurement begin switch to be pressed (step SP10 (FIG. 7)). Here, as shown in FIG. 4, the operator applies ultrasonic gel 14 over the surface of the soft tissue Ma (skin surface X) on the cortical bone Mb at the patient measuring location, presses the transducer 1 against the skin surface X via the ultrasonic gel 14, and turns the measurement begin switch on, with the transducer surface facing the cortical bone Mb. When the measurement begin switch is turned on (step SP11), the CPU 11 writes "1" to the measurement continue flag to raise the measurement continue flag, and the diagnostic operations are then started according to the processing procedure (primarily the procedure in the maximum echo level extraction subprogram) shown in FIG. 7. The CPU 11 first issues a 1 pulse generating command to the pulse generator 4 (step SP12). When the pulse generator 4 receives the 1 pulse generating command from the CPU 11, it sends an electrical pulse signal to the transducer 1. When the transducer 1 receives the electrical pulse signal from the pulse generator 4, it emits a nearly flat ultrasonic pulse Ai toward the patient's cortical bone Mb. As shown in FIG. 5, the ultrasonic pulse Ai thus emitted is introduced from the skin surface X into the soft tissue Ma and is propagated toward the cortical bone Mb. A portion is reflected at the surface Y of the cortical bone Mb, resulting in echo Ae, and a portion is absorbed by the cortical bone Mb, but the remainder passes through the cortical bone Mb. The echo Ae follows a path opposite that of the incident ultrasonic pulse Ai and is received back at the ultrasonic oscillator 1a of the transducer 1. When the ultrasonic pulse Ai is emitted from the transducer 1 toward the cortical bone Mb, as shown in the figure, first the transmission resonance $An_1$, then the echo $An_2$ from the skin surface X, and a little later the echo Ae from the cortical bone Mb are received by the ultrasonic oscillator 1a and are converted to a reception signal (electrical signal) corresponding to the ultrasonic waveform and amplitude. The resulting reception signal is input via the cable 3 to the apparatus main unit 2 (matching circuit 5), amplified to a predetermined amplification level by the amplifier 6, shaped into a linear waveform by the waveform shaper 7, and then input to the A/D convertor 8.

After the CPU 11 has sent a 1 pulse generating command to the pulse generator 4 (step SP12), it issues a sampling start command (step SP13) to the A/D convertor 8 upon measuring the time in which the transmission resonance $An_1$ is received by the ultrasonic oscillator 1a of the transducer 1, the echo $An_2$ from the skin surface X is then received, and the echo Ae from the cortical bone Mb returns to the transducer surface of the oscillator 1a of the transducer 1.

When the A/D convertor 8 receives the sampling start command from the CPU 11, it samples the reception signal for one echo from the cortical bone Mb, which has been input after undergoing waveform shaping from the waveform shaper 7, at a predetermined frequency (such as 12 MHz) to convert it to a digital signal, and the resulting N sample value (digital signal for 1 echo) is temporarily stored in the sample memory itself. Subsequently, when there is a transmission command from the CPU 11, the N sample values stored in the sampling memory are sequentially transmitted to the CPU 11. The CPU 11 sequentially takes in the N sample values from the A/D convertor 8 and stores the current echo waveform in the echo waveform memory area of RAM 10, the maximum value among the N sample values is extracted so as to detect the current echo level, and the detected results are stored in the echo level memory area of RAM 10 (step SP14). The current echo level stored in the echo level memory area of RAM 10, as shown by the broken line in FIG. 4, is displayed by the deflection of the liquid crystal needle pattern 12a in the level meter 12 (step SP15).

The CPU 11 then reads out the current echo level and the maximum echo level from the echo level memory area of RAM 10 to determine whether or not the current echo level value is greater than the maximum echo level value (step SP16). This is the first determination, and since the maximum echo level value is the initialized value "0," the CPU 11 determines that the current echo level value is greater than the maximum echo level value, the maximum echo level value stored in the echo level memory area of RAM 10 is replaced by the current echo level value, and the maximum echo waveform stored in the echo waveform memory area of RAM 10 is also replaced by the current echo waveform (step SP17). The new maximum echo waveform is displayed on the screen of the display 13, and the new maximum echo level is displayed by the deflection of the liquid crystal needle pattern 12b on the level meter 12, as shown by the solid line in FIG. 4 (step SP18). Then, when the CPU 11 looks for the measurement continue flag in RAM 10 (step SP19) and raises the measurement continue flag (when the contents of the measurement flag are "1"), the CPU 11 determines that measurement is to continue, repeats the 1 pulse emission and 1 echo reception described above (steps SP12 through SP15), and then again reads out the current echo level and maximum echo level from the echo level memory area in RAM 10 in step SP16 to determine whether or not the current echo level value is greater than the value of the maximum echo level. When it is determined that the current echo level is not greater than the maximum echo level, the system jumps directly to step SP19 without modifying the values, and looks for the measurement continue flag. As long as the operator does not press the measurement end switch, the contents of the measurement continue flag are "1," and the CPU 11 repeats the 1 pulse emission 1 echo transmission described above (steps SP12 through SP15) and the maximum echo level extraction (steps SP16 through SP19).

While the CPU 11 is repeating the process described above (steps SP12 through SP19), the operator aims the transducer 1 at the skin surface X, as indicated by the arrow W in FIG. 4, and changes the direction of the transducer 1 by sometimes describing a circle in the manner of the precession of a top and sometimes oscillating it in any direction in the manner of a seesaw on the cortical bone Mb at the measuring site while checking the direction in which the liquid crystal needle patterns 12a and 12b of the level meter 12 oscillate the greatest, that is, the direction in which the maximum echo level is detected. As shown in FIG. 6(a), the maximum oscillation of the liquid crystal needle patterns 12a and 12b of the level meter 12 is where the normal of the cortical bone Mb and the normal of the transducer surface of the transducer 1 are aligned and thus when the wavefront of the flat ultrasonic pulse Ai is roughly parallel to the surface Y of the cortical bone Mb (when the flat ultrasonic pulse Ai lands roughly perpendicular on the surface Y of the cortical bone Mb).

That is because, when both normals are aligned, as shown in FIG. 6(a), the echo Ae reflected perpendicular on the surface Y of the cortical bone Mb returns perpendicular to the transducer surface of the transducer 1, so the wavefront of the echo Ae is also roughly parallel to the transducer surface. There is thus minimal deviation of the echo Ae phase due to differences in the reception position on the transducer surface, so the crests and troughs of the reception signal do not cancel each other out very much, allowing echoes Ae to be received at maximum echo levels. In contrast, when both normals are not aligned, as shown in FIG. 6(b), the wavefront of the echo Ae does not line up with the transducer surface, so the reception signal is lower because the crests and troughs cancel each other out.

Diagnostic accuracy is increased in the diagnostic apparatus in this embodiment, based on the extraction of the perpendicularly reflected echo Ae. That is because Formula (5) for deriving the acoustic impedance Zb from the ultrasonic reflection coefficient R during roughly perpendicular reflection in the acoustic impedance calculating subprogram described above is established when the echo Ae is reflected roughly perpendicularly from the cortical bone Mb, as described above. Hence, when the echo level peaks out as the operator varies the angle of the transducer 1 around the normal of the cortical bone Mb, it can be concluded that echoes Ae are reflected roughly perpendicularly on the surface Y of the cortical bone Mb back to the transducer surface of the transducer 1.

The liquid crystal patterns 12a and 12b of the level meter 12 change in a sensitive manner (oscillate vigorously) in the event of pronounced nonalignment between the normal of the cortical bone Mb and the normal of the transducer surface, but since such changes are blunted (the oscillation abates) when the normals are roughly aligned, it is relatively easy to find a perpendicularly reflected echo Ae.

When the operator looks at the extent of oscillation in the liquid crystal needle patterns 12a and 12b of the level meter and determines that the maximum echo level can be extracted, the measurement end switch is pressed. When the measurement end switch is pressed, the CPU 11 rewrites the contents of the measurement continue flag as "0" by an interrupt process so as to lower the measurement continue flag. When the measurement continue flag is lowered, the CPU 11 stops any subsequent 1 pulse emissions (step SP19). The maximum echo level stored in the echo level memory area of RAM 10 is read out and displayed on the screen of the display 13 (step SP20).

The CPU 11 then executes the reflection coefficient calculating subprogram to calculate the ultrasonic reflection coefficient R at the interface between the soft tissue Ma and cortical bone Mb of the patient based on the maximum echo level V1 stored in the echo level memory area of RAM 10 and the complete echo level V0 previously written to the reflection coefficient calculating subprogram (step SP21), and the calculated value is displayed on the screen of the display 13 (step SP22).

Here, the ultrasonic reflection coefficient R is derived from the ratio [R=V1/V0] between the complete echo level V0 during completely perpendicular reflection and the maximum echo level V1. The complete echo level V0 can be calculated theoretically, but it can also be determined by preparing a dummy block made of plastic or the like to measure the echo levels.

The CPU 11 then substitutes the value for the ultrasonic reflection coefficient R given by the reflection coefficient calculating subprogram into Formula (5) to calculate the acoustic impedance Zb [kg/m²sec] of the cortical bone Mb in accordance with the acoustic impedance calculating subprogram (step SP23), and the results of the calculation are displayed on the screen of the display 13 (step SP24). The CPU 11 then substitutes the value for the acoustic impedance Zb of the cortical bone Mb given by the acoustic impedance calculating subprogram into Formula (7) to calculate the bone density in accordance with the bone density calculating subprogram (step SP25), and the results of the calculation are displayed on the screen of the display 13 (step SP26).

Thus, in the structure described above, the maximum echo level is easily extracted, with good extraction reproducibility, because of the use of perpendicularly reflected echoes Ae in which the changes in echo levels from the cortical bone due to displacement (oscillation of the transducer 1) are blunted. Because the cortical bone of the lower tibia is used as a measuring location, there is less contamination by noise of unknown origin, thus ensuring reliable detection of echoes from the cortical bone. In addition, the current echo levels are displayed moment by moment by the liquid crystal needle pattern 12a of the level meter 12, and the maximum echo level is also constantly displayed by the liquid crystal needle pattern 12b, so the maximum echo level is easy to find. The acoustic impedance Zb of the cortical bone Mb can thus also be accurately determined.

The acoustic impedance Zb of the cortical bone Mb is expressed by the square root of the [elastic modulus× density] of cortical bone Mb, and thus increases with extreme sensitivity in response to increases in the cortical bone density as a result of the synergistic effects in which the elastic modulus of cortical bone increases as the cortical bone density increases. Similarly, the elastic modulus of cortical bone decreases with decreases in cortical bone density, so the acoustic impedance Zb decreases with extreme sensitivity in response to decreases in cortical bone density. The acoustic impedance Zb of cortical bone Mb is thus a good index for determining bone density.

Furthermore, a recurrence formula for bone density ρ relative to acoustic impedance Zb has also been prepared, allowing the bone density (cortical bone density) ρ of a patient to be calculated with a 95% reliability based on the acoustic impedance Zb. The extent of osteoporosis can thus be directly ascertained.

Embodiment 2

A second embodiment of the present invention is described below.

The reflection coefficient calculating subprogram (algorithm) used in the second embodiment is different from that in the first embodiment described above. Other than this, the embodiment is roughly the same in structure as the first embodiment. That is, in the reflection coefficient calculating subprogram in the second embodiment, the ultrasonic reflection coefficient R for when the ultrasonic pulse Ai is roughly perpendicularly reflected at the interface between the soft tissue Ma and cortical bone Mb can be determined using Formula (10), assuming that the ultrasonic pulse Ai and echo Ae are regarded as being sufficiently flat and that the attenuation of the ultrasonic waves in the soft tissue Ma can be disregarded.

$$R = Ve/P \cdot Q \cdot B \cdot Vi \qquad (10)$$

R: ultrasonic reflection coefficient for when ultrasonic pulse Ai is roughly perpendicularly reflected at the interface between soft tissue Ma and cortical bone Mb P: sound pressure of ultrasonic pulse Ai output from transducer 1 in roughly perpendicular direction When unit electrical signal (voltage, current, scattering parameter, or the like) is applied to transducer 1

Q: amplitude of reception signal (electrical signal) output from transducer 1 when unit sound pressure of echo Ae lands roughly perpendicular on transducer surface of transducer 1

B: product of amplification level amplifier 6 and amplification level of waveform shaper 7

Vi: amplitude of electrical signal applied from pulse generator 4 to transducer 1

Ve: maximum echo level

P, Q, B, and Vi are all functions of frequency. Components at a central frequency (such as 2.5 MHz) are used here. The measured and set values for P, Q, B, and Vi are previously written to ROM 9 (the reflection coefficient calculating subprogram in this example).

Formula (10) is derived as follows. First, when an electrical signal of amplitude Vi is applied from the pulse generator 4 to the transducer 1, an ultrasonic pulse Ai of sound pressure PVi is output from the transducer surface of the transducer 1 toward the cortical bone Mb. As a result, a bone echo Ae of sound pressure RPVI is returned perpendicularly to the transducer surface of the transducer 1. The maximum echo level Ve is accordingly given by Formula (11).

$$Ve = Q \cdot R \cdot P \cdot B \cdot Vi \tag{11}$$

Formula (10) is derived from Formula (11).

Roughly the same effects as those in the first embodiment can thus also be obtained in the second embodiment because the acoustic impedance Zb of cortical bone Mb is calculated by the CPU 11 from the ultrasonic reflection coefficient R at the interface between soft tissue Ma and cortical bone Mb.

Embodiment 3

A third embodiment of the present invention is described below.

The third embodiment differs from the first embodiment in that $\rho min$ to $\rho max$ is calculated and output with a 95% reliability or 5% significance level when the bone density calculating subprogram is executed to carry out the regression of the bone density $\rho$. Other than this, the embodiment is roughly the same in structure as the first embodiment. That is, Formula (12) is used as a recurrence formula giving the bone density $\rho$ in the bone density calculating subprogram in this example.

$$\rho = \alpha Zb + \beta \tag{12}$$

$\rho$: cortical bone density [kg/m$^3$]

Zb: acoustic impedance of cortical bone (kgm$^2$sec]

$\alpha$: regression coefficient [sec/m]

$\beta$: section [kg/m$^3$]

Formula (12) differs from Formula (5) in the first embodiment described above in that the value of the regression coefficient a has a wider range from $1.27 \times 10^{-4}$ to $2.34 \times 10^{-4}$, and the value for section $\beta$ has a wider range from 646 to 887.

As such, the bone density $\rho min$ to $\rho max$ that is determined is also wider.

$$\rho min = 1.27 \times 10^{-4} Zb + 646 \tag{13}$$
$$= (1.80 \times 10^{-4} + 30\%) Zb + (766 + 16\%)$$

$$\rho max = 2.34 \times 10^{-4} Zb + 887 \tag{14}$$
$$= (1.80 \times 10^{-4} + 30\%) Zb + (766 + 16\%)$$

Expressed in percentage, Formulas (13) and (14) are the same as Formulas (8) and (9) in the first embodiment, and it may be seen that the recurrence formula in the first embodiment is the equivalent of the centerline of the wider range of the recurrence formula in the third embodiment. As a result, the patient's bone density $\rho$ has a 95% probability (reliability) and 5% significance level of falling within the $\rho min$ to $\rho max$ range when the acoustic impedance Zb value for the cortical bone of any patient is Zb. The same specimen analysis data as that used in the first embodiment is used to derive the recurrence formula in the third embodiment, so the bone density $\rho$ calculated by X-ray (QCT) has a high correlation (r=0.67) with the acoustic impedance Zb in the third embodiment as well.

Thus, roughly the same effects as in the first embodiment above can be obtained with the structure of this example, allowing the estimated value of the bone density $\rho$ to be assessed in terms of probability (statistics).

Embodiment 4

A fourth embodiment of the present invention is described below.

Figure 9:
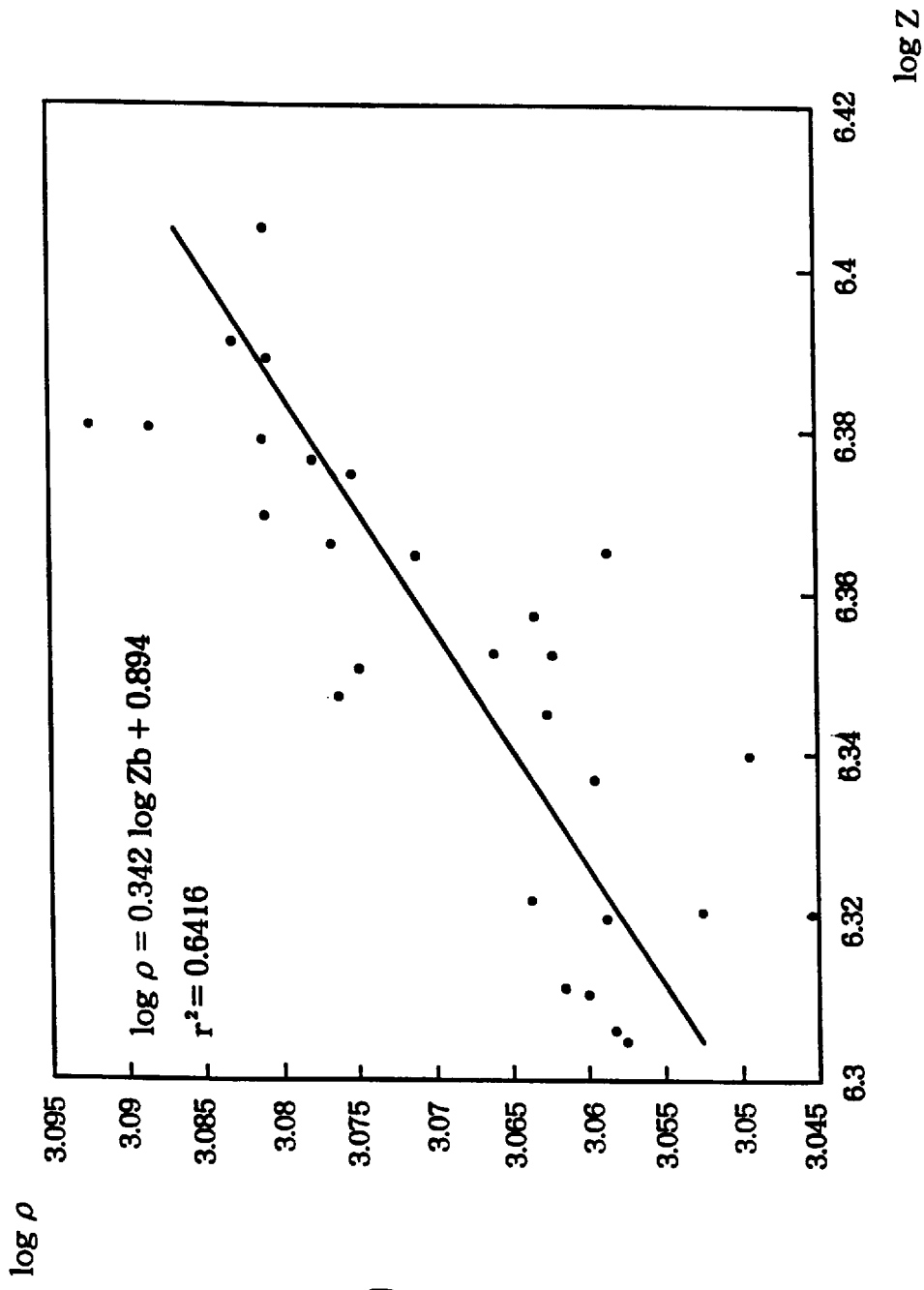
FIG. 9 is a graph of the regression line for cortical bone density $\rho$ relative to the acoustic impedance Zb, and is used to describe the contents of the bone density calculating subprogram in a fourth embodiment.

The structure of the fourth embodiment differs substantially from the structure of the first through third embodiments in that a linear recurrence formula ($\rho = \alpha Zb + \beta$) was used in the bone density calculating subprograms of the first through third embodiments, whereas a nonlinear recurrence formula, as indicated in Formula (15), is used in the fourth embodiment. Here, Formula (15) is a recurrence formula for bone density $\rho$ relative to the acoustic impedance Zb, and, as shown in FIG. 9, is obtained by the statistical treatment of data from the specimen examination.

$$\rho = BZb^A = 10^{0.894} Zb^{0.342} \tag{15}$$

$\rho$: cortical bone density [kg/m$^3$]

Zb: acoustic impedance of cortical bone [kg/m$^2$sec]

A: regression index

B: constant [sec/m]

Statistical hypothesis testing resulted in a 95% probability (reliability) that a patient's bone density $\rho$ would fall within the $\rho min$ to $\rho max$ range when the value for the acoustic impedance Zb of the cortical bone of any patient is Zb. The significance level is thus 5%. Here, $\rho min$ is given by Formula (16), and $\rho max$ is given by Formula (17).

$$\rho min = 10^{(0.894-73\%)} Zb^{(0.342-30\%)} \tag{16}$$

$$\rho max = 10^{(0.894+73\%)} Zb^{(0.342+30\%)} \tag{17}$$

The same specimen analysis data as that used in the first embodiment is used to derive the recurrence formula in the fourth embodiment, so the bone density $\rho$ calculated by X-ray (QCT) has a high correlation (r=0.67) with the acoustic impedance Zb in the fourth embodiment as well. Thus, roughly the same effects as in the first embodiment above can be obtained with the structure of this example.

Embodiment 5

The fifth embodiment differs from the fourth embodiment in that $\rho min$ to $\rho max$ is calculated and output with a 95% reliability or 5% significance level when the bone density calculating subprogram is executed to carry out the regression of the bone density $\rho$. Other than this, the embodiment is roughly the same in structure as the fourth embodiment. That is, Formula (18) is used as a recurrence formula giving the bone density $\rho$ in the bone density calculating subprogram in this example.

$$\rho = BZb^A = 10^{0.894} Zb^{0.342} \tag{18}$$

$\rho$: cortical bone density [kg/m$^3$]

Zb: acoustic impedance of cortical bone [kg/m$^2$sec]

A: regression index

B: constant [sec/m]

Formula (18) differs from Formula (15) in the fourth embodiment in that the value of the regression index A has a wider range of 0.239 to 0.445, and the value of the constant B also has a wider range of $10^{0.239}$ to $10^{1.55}$. As such, the bone density ρmin to ρmax that is determined also has a wider range.

$$\rho min = 10^{0.239} Zb^{0.239} \qquad (19)$$
$$= 10^{(0.894-73\%)} Zb^{(0.342-30\%)}$$
$$\rho max = 10^{1.55} Zb^{0.445} \qquad (20)$$
$$= 10^{(0.894+73\%)} Zb^{(0.342+30\%)}$$

Expressed in percentage, Formulas (19) and (20) are the same as Formulas (16) and (17) in the fourth embodiment, and it may be seen that the recurrence formula in the fourth embodiment is the equivalent of the centerline of the wider range of the recurrence formula in the fifth embodiment. As a result, the patient's bone density ρ has a 95% probability (reliability) and 5% significance level of falling within the ρmin to ρmax range when the acoustic impedance Zb value for the cortical bone of any patient is Zb. The same specimen analysis data as that used in the first embodiment is used to derive the recurrence formula in the fifth embodiment, so the bone density ρ calculated by X-ray (QCT) has a high correlation (r=0.67) with the acoustic impedance Zb in the fifth embodiment as well.

Thus, roughly the same effects as in the first embodiment above can be obtained with the structure of this example, allowing the estimated value of the bone density ρ to be assessed in terms of probability (statistics).

Embodiment 6

A sixth embodiment of the present invention is described below.

Figure 10:
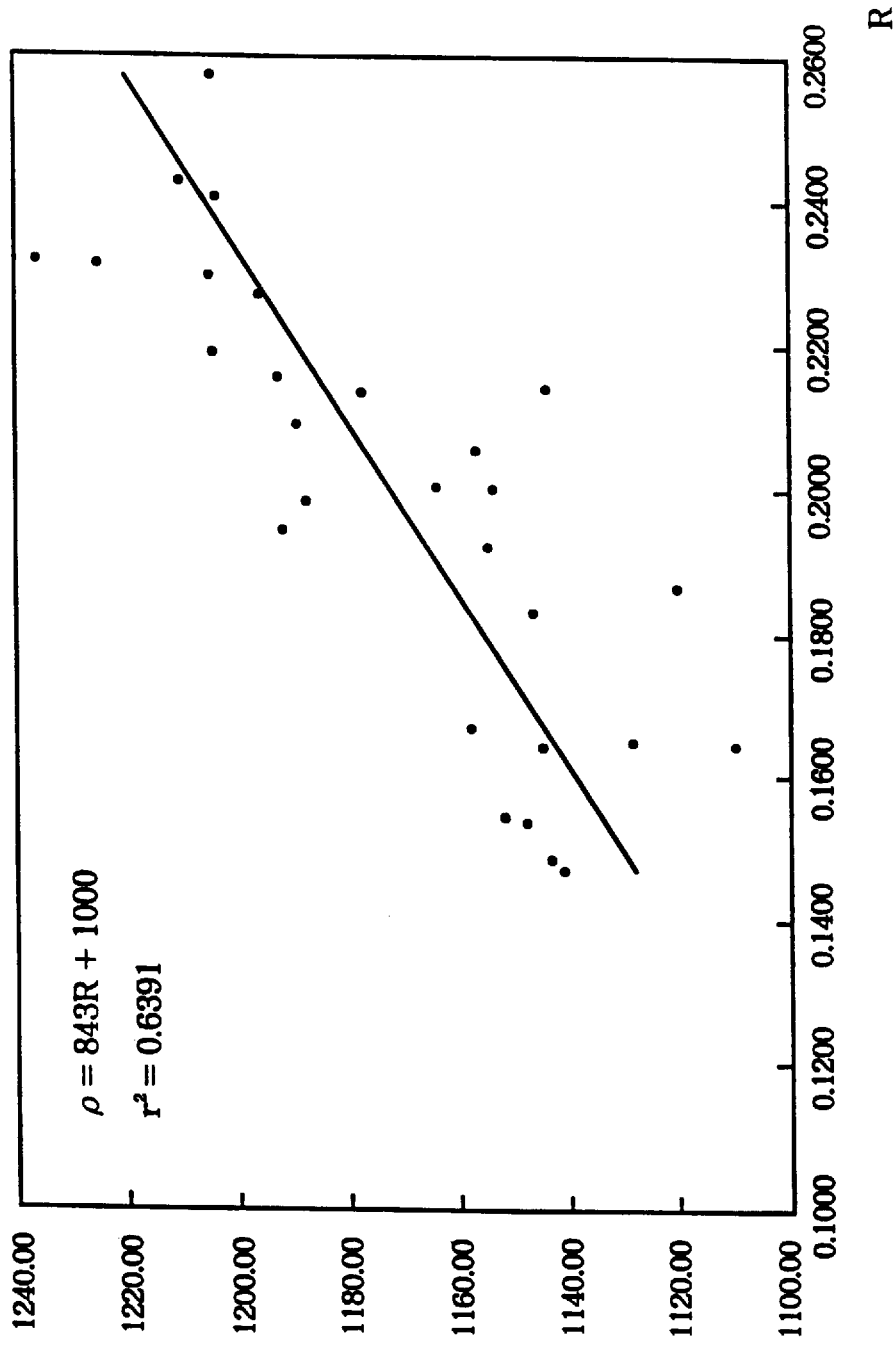
FIG. 10 is a graph of the regression line for cortical bone density $\rho$ relative to the acoustic impedance Zb, and is used to describe the contents of the bone density calculating subprogram in a sixth embodiment.

The structure of the sixth embodiment differs substantially from the structure of the first through fifth embodiments in that the patient's bone density is calculated using a predetermined recurrence formula for bone density ρ relative to acoustic impedance Zb in the bone density calculating subprogram in the first through fifth embodiments, whereas the patient's bone density ρ is calculated using a recurrence formula for bone density ρ relative to the ultrasonic reflection coefficient R in the bone density calculating program in the sixth embodiment. Here, Formula (21) is a recurrence formula for bone density ρ relative to the ultrasonic reflection coefficient R, and, as shown in FIG. 10, is obtained by the statistical treatment of data from the specimen examination.

$$\rho = \alpha' R + \beta' = 843R + 1000 \qquad (21)$$

ρ: cortical bone density [kg/m³]
R: ultrasonic reflection coefficient at interface between soft tissue and cortical bone
α': regression coefficient [kg/m³]
β': section [kg/m³]

In the specimen examination described above, the ultrasonic reflection coefficient R was calculated for the cortical bone of the tibia using ultrasonic reflection, and the density ρ of the cortical bone Mb was determined by X-ray (QCT) of the radius (arm bone). Specimen analysis revealed that the bone density measured by X-ray (QCT) had a high correlation (r=0.67) with the ultrasonic reflection coefficient R.

Statistical hypothesis testing resulted in a 95% probability (reliability) that a patient's bone density ρ would fall within the ρmin to ρmax range when the value for the ultrasonic reflection coefficient R of the cortical bone of any patient is R. The significance level is thus 5%.

Here, ρmin and ρmax are given by Formulas (22) and (23), respectively.

$$\rho min = (843-30\%)R + (1000-6\%) \qquad (22)$$
$$\rho min = (843+30\%)R + (1000+6\%) \qquad (23)$$

The same specimen analysis data as that used in the first embodiment is used to derive the recurrence formula in the sixth embodiment, so the bone density ρ calculated by X-ray (QCT) has a high correlation (r=0.67) with the acoustic impedance Zb in the sixth embodiment as well. Thus, roughly the same effects as in the first embodiment above can be obtained using the ultrasonic reflection coefficient R at the interface between the soft tissue Ma and cortical bone Mb, which is a monotone increasing function of the acoustic impedance Zb of cortical bone Mb, as an index of bone density instead of using the acoustic impedance Zb of cortical bone MB as an index of bone density ρ.

Embodiment 7

The seventh embodiment differs from the sixth embodiment in that ρmin to ρmax is calculated and output with a 95% reliability or 5% significance level when the bone density calculating subprogram is executed to carry out the regression of the bone density ρ. Other than this, the embodiment is roughly the same in structure as the sixth embodiment. That is, Formula (24) is used as a recurrence formula giving the bone density ρ in the bone density calculating subprogram in this example.

$$\rho = \alpha' R + \beta' \qquad (24)$$

ρ: cortical bone density [kg/m³]
R: ultrasonic reflection coefficient at interface between soft tissue and cortical bone
α': regression coefficient [kg/m³]
β': section [kg/m³]

Formula (24) differs from Formula (21) in the sixth embodiment in that the value of the regression coefficient α' has a wider range from 588 to 1100, and the value for section β' has a wider range from 953 to 1060. As such, the bone density ρmin to ρmax that is determined is also wider.

$$\rho min = 588Zb + 953 \qquad (25)$$
$$= (843-30\%)R + (100-6\%)$$
$$\rho max = 1100Zb + 1060 \qquad (26)$$
$$= (843-30\%)R + (1000+6\%)$$

Expressed in percentage, Formulas (25) and (26) are the same as Formulas (22) and (23) in the sixth embodiment, and it may be seen that the recurrence formula in the sixth embodiment is the equivalent of the centerline of the wider range of the recurrence formula in the seventh embodiment. As a result, the patient's bone density ρ has a 95% probability (reliability) and 5% significance level of falling within the ρmin to ρmax range when the acoustic impedance Zb value for the cortical bone of any patient is Zb. The same specimen analysis data as that used in the first embodiment is used to derive the recurrence formula in the seventh embodiment, so the bone density ρ calculated by X-ray (QCT) has a high correlation (r=0.67) with the acoustic impedance Zb in the seventh embodiment as well. Thus, roughly the same effects as in the first embodiment above can be obtained with the structure of this example, allowing the estimated value of the bone density ρ to be assessed in terms of probability (statistics).

Embodiment 8

Figure 11:
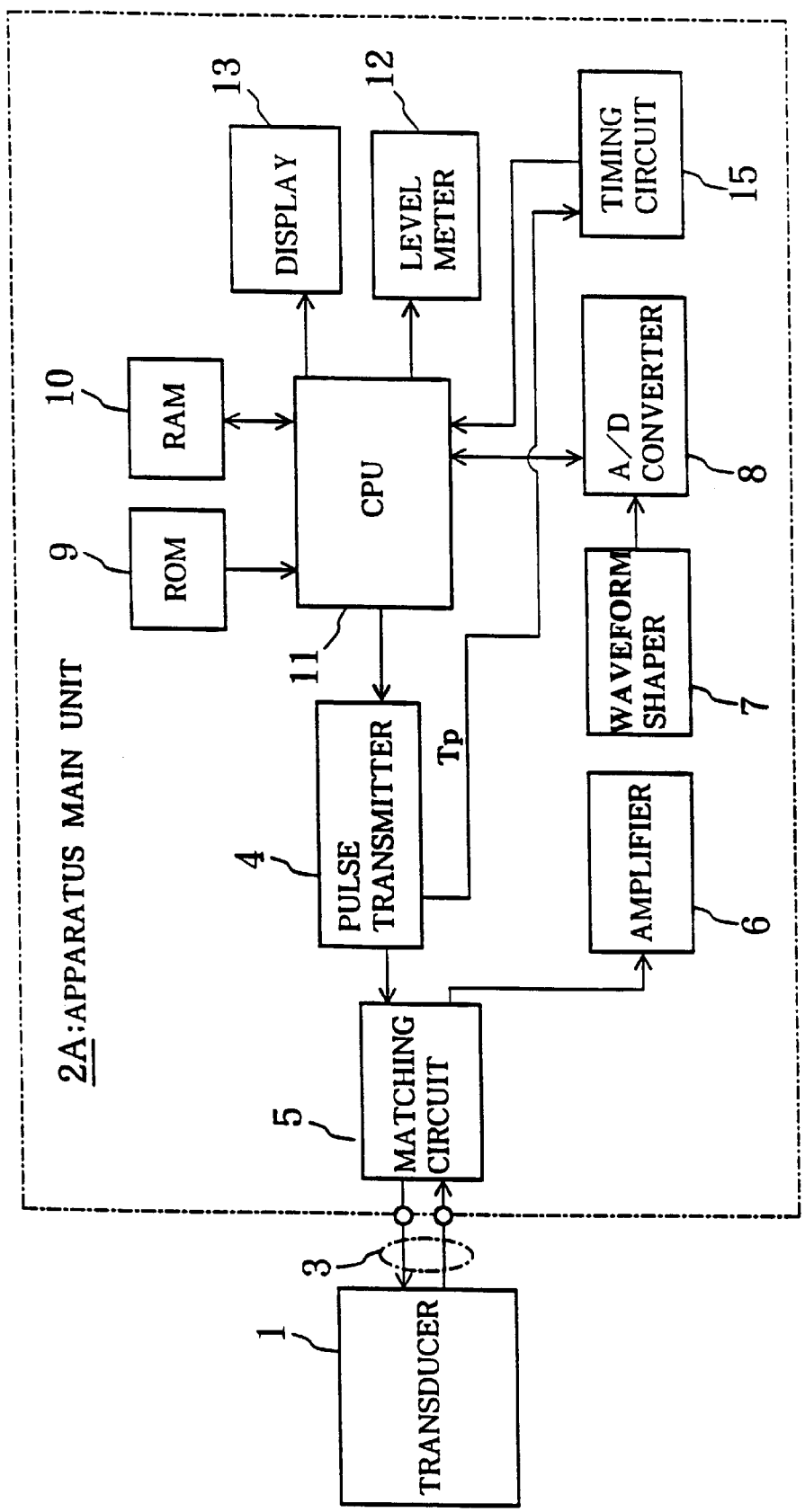
FIG. 11 is a block diagram of the electrical structure of the apparatus for diagnosing osteoporosis in an eighth embodiment of the present invention.
Figure 12:
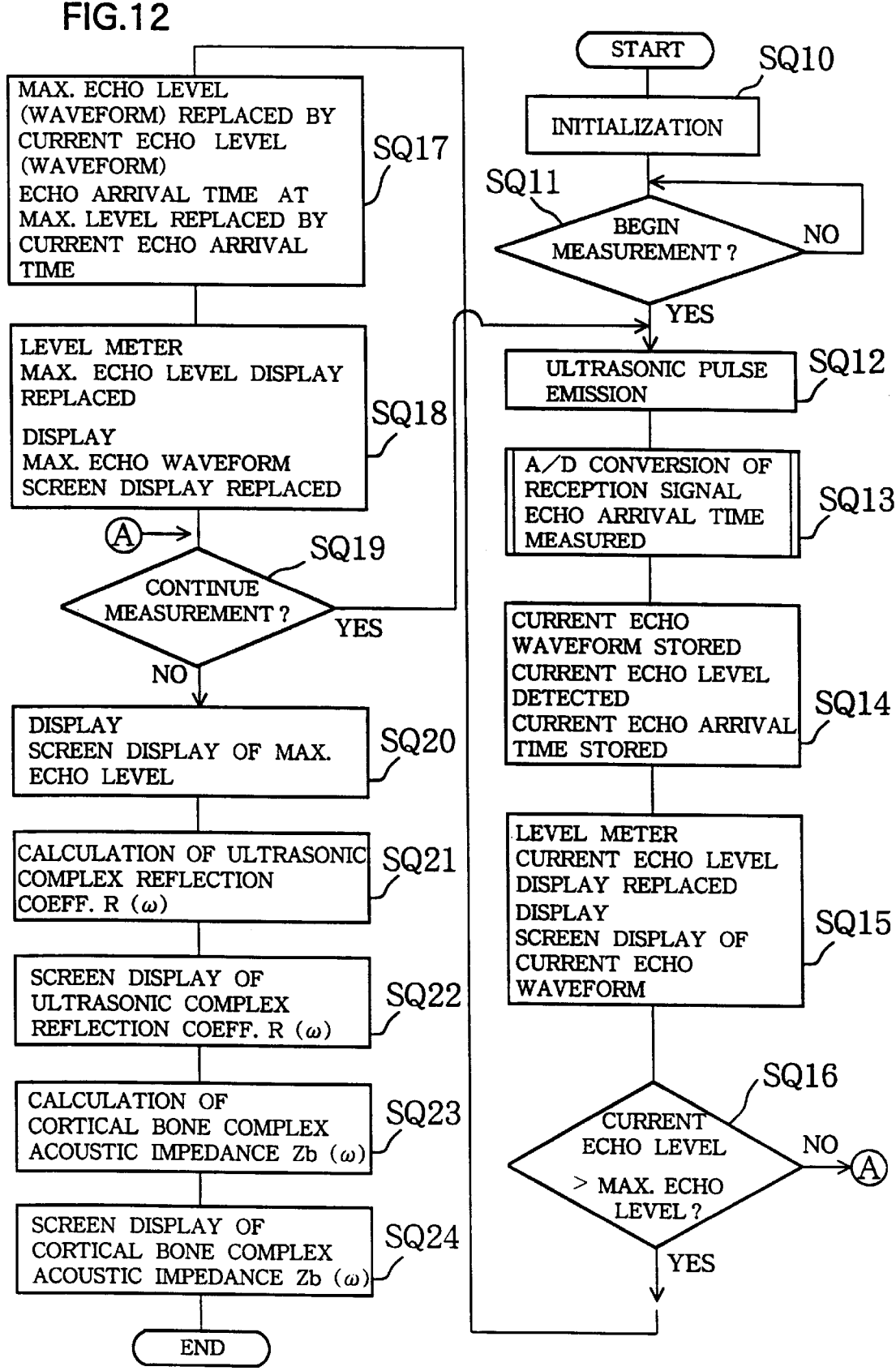
FIG. 12 is a flow chart of the operation and processing procedures of the same apparatus.

FIG. 11 is a block diagram of the electrical structure of the apparatus for diagnosing osteoporosis in an eighth embodiment of the present invention, and FIG. 12 is a flow chart of the operation and processing procedures of the same apparatus.

The structure of the apparatus for diagnosing osteoporosis in the eighth embodiment differs substantially from the structure of the first through seventh embodiments described above by having a Fourier transform function, allowing the complex acoustic impedance to be calculated.

As shown in FIG. 11, the apparatus main unit 2A in this example has a new timing circuit 15 in addition to the structure of the first embodiment.

The pulse generator 4 repeatedly produces an electrical pulse signal of 1 MHz or 2.5 MHz, for example, at a predetermined period (100 msec, for example) and transmits these pulses to the transducer 1, and a timing start signal Tp is supplied to the timing circuit 15 with the same timing as that in the transmission of the electrical pulse signal. The ultrasonic pulse period is set sufficiently longer than the echo arrival time described below.

The following processing program is stored in the ROM 9 in this example to allow the CPU 11 to calculate the complex acoustic impedance in order to diagnose osteoporosis. That is, the processing program in this example includes: a procedure in which the echo waveform (echo signal) is taken from the A/D converter 8 for each pulse and echo so as to check the echo level; a procedure in which the maximum echo level is extracted from the many echo levels thus detected; a processing procedure in which the high speed Fourier transform means is actuated to rapidly determine the maximum echo waveform spectrum on the basis of the maximum echo waveform during the extraction of the maximum echo level; a procedure in which the ultrasonic complex reflection coefficient $R(\omega)$ of the cortical bone Mb relative to the soft tissue Ma of the patient at an angular frequency $\omega$ is calculated based on the spectrum; and a procedure in which the complex acoustic impedance $Zb(\omega)$ of the patient's cortical bone Mb at an angular frequency $\omega$ is calculated based on the ultrasonic complex reflection coefficient $R(\omega)$ thus calculated.

In this processing program, the complex acoustic impedance $Zb(\omega)$ for the patient's cortical bone Mb is given by Formula (27).

$$Zb(\omega)=Za(\omega)\{R)\omega)+1\}/\{1-R(\omega)\} \quad (27)$$

$Za(\omega)$: complex acoustic impedance (known) of soft tissue Ma at angular frequency $\omega$ $R(\omega)$: ultrasonic complex reflection coefficient of cortical bone Mb relative to soft tissue Ma of patient at angular frequency $\omega$ Formula (27) is derived from Formula (28). That is, as shown in FIG. 6(a), the ultrasonic complex reflection coefficient $R(\omega)$ of the cortical bone Mb relative to the soft tissue Ma of the patient is expressed by Formula (28) when the surface Y of the cortical bone Mb is roughly flat, the ultrasonic pulse Ai emitted from the transducer 1 is also flat, and the wavefront is roughly parallel to the surface Y of the cortical bone Mb (in other words, when the ultrasonic pulse Ai lands roughly perpendicular on the surface Y of the cortical bone Mb). Meanwhile, the echo level is greatest when the ultrasonic pulse Ai lands roughly perpendicular on the surface Y of the cortical bone Mb. As such, the ultrasonic complex reflection coefficient $R(\omega)$ given by Formula (28) is the ultrasonic complex reflection coefficient $R(\omega)$ when the maximum echo level is obtained. Formula (27) is thus obtained by the rearrangement of Formula (28).

$$R(\omega)=\{Zb(\omega)-Za(\omega)\}/\{Zb(\omega)+Za(\omega)\} \quad (28)$$

The CPU 11 uses RAM 10 to execute the processing program described above stored in ROM 9 so as to start the pulse generator 4 or A/D convertor 8, controls each component of the apparatus to take in an echo signal from the A/D convertor 8 for each pulse and echo to detect the echo level, extracts the maximum echo level, determines the maximum echo waveform spectrum based on the maximum echo waveform, calculates the ultrasonic complex reflection coefficient $R(\omega)$ of the cortical bone Mb relative to the soft tissue Ma of the patient at an angular frequency ($\omega$) on the basis of the spectrum, calculates the complex acoustic impedance $Zb(\omega)$ of the patients' cortical bone Mb at the angular frequency $\omega$ based on the ultrasonic complex reflection coefficient $R(w)$ thus calculated, and produces a diagnosis of osteoporosis on the basis of the phase data and amplitude data obtained form the complex acoustic impedance thus calculated. The measured values of the echo levels and the like, the ultrasonic complex reflection coefficient $R(\omega)$, the complex acoustic impedance $Zb(\omega)$, the calculated value for bone density $\rho$, the echo waveform, and the like are displayed on the screen of the display 13 under the control of the CPU 11. The timing circuit 15 measures the echo arrival time, which is the time elapsed after the ultrasonic pulse Ai is emitted from the transmitting surface of the transducer 1 until the echo Ae is reflected on the surface Y of the cortical bone Mb back to the receiving surface. The timing circuit 15 comprises a clock generator and counter circuit which are not shown in the figure, wherein the timing is started whenever a timing start signal Tp is received from the pulse generator 4, and the timing is concluded when a stop signal is sent from the A/D convertor 8. Here, the transmission of the stop signal from the A/D convertor 8 is the timing by which the A/D convertor 8 detects the reception of the echo Ae. The timing value is thus kept until it is reset, and the timing value that is kept is given to the CPU 11 as the echo arrival time as needed.

The operation of this example (primarily the CPU 11 processing during the diagnosis of osteoporosis) is described below with reference to FIG. 12.

First, the cortical bone Mb of the tibia, for example, which has a substantial curvature radius, which is close to the surface of the skin, and which is relatively thick, is selected as the measuring site.

When the power source is turned on in the apparatus, the CPU 11 presets the various components of the apparatus and initializes the counter, the various registers, and the various flags (step SQ10), and then waits for the measurement begin switch to be pressed (step SQ11). Here, as shown in FIG. 4, the operator applies ultrasonic gel 14 over the surface of the soft tissue Ma (skin surface X) on the cortical bone Mb at the patient measuring location, presses the transducer 1 against the skin surface X via the ultrasonic gel 14, and turns the measurement begin switch on, with the transducer surface facing the cortical bone Mb. When the measurement begin switch is turned on (step SQ11), the CPU 11 writes "1" to the measurement continue flag to raise the measurement continue flag, and the diagnostic operations are then started according to the processing procedure given in FIG. 12.

The CPU 11 first issues a 1 pulse generating command to the pulse generator 4 (step SQ12). When the pulse generator 4 receives the 1 pulse generating command from the CPU 11, it sends an electrical pulse signal to the transducer 1, and a timing start signal Tp is supplied to the timing circuit 15 with the same timing as the transmission of the ultrasonic pulse.

When the transducer 1 receives the electrical pulse signal from the pulse generator 4, it emits an ultrasonic pulse Ai (which may be regarded as being flat during the short period of treatment) toward the patient's cortical bone Mb. Meanwhile, the timing circuit 15 begins timing at the same time that the timing start signal Tp is received from the generator 4. As shown in FIG. 5, a portion of the ultrasonic pulse Ai thus emitted from the transducer 1 is reflected at the surface X of the skin, and the remainder is introduced from the surface X of the skin into the soft tissue Ma and is propagated toward the cortical bone Mb. A portion is reflected at the surface Y of the cortical bone Mb, resulting in echo Ae, and a portion is absorbed by the cortical bone Mb, while the remainder passes through the cortical bone Mb. The echo Ae from the cortical bone Mb follows a path opposite that of the incident ultrasonic pulse Ai and is received back at the ultrasonic oscillator 1a of the transducer 1. After the emission of the ultrasonic pulse Ai by the transducer 1, first the transmission resonance $An_1$, then the echo $An_2$ from the skin surface X, and a little later the echo Ae from the cortical bone Mb are received by the ultrasonic oscillator 1a and are converted to a reception signal corresponding to the ultrasonic waveform and amplitude. The resulting reception signal is input via the cable 3 to the apparatus main unit 2 (matching circuit 5), amplified to a predetermined amplification level by the amplifier 6, shaped into a linear waveform by the waveform shaper 7, and then input to the A/D convertor 8.

After the CPU 11 has sent a 1 pulse generating command to the pulse generator 4 (step SQ12), it issues a sampling start command (step SQ13) to the A/D convertor 8 upon measuring the time in which the transmission resonance $An_1$ is received by the ultrasonic oscillator 1a of the transducer 1, the echo $An_2$ from the skin surface is then received, and the echo Ae from the cortical bone Mb returns to the transducer surface of the ultrasonic oscillator 1a of the transducer 1. When the A/D convertor 8 receives the sampling start command from the CPU 11, it samples the reception signal for one echo from the cortical bone Mb, which has been input after undergoing waveform shaping from the waveform shaper 7, at a predetermined frequency (such as 12 MHz) to convert it to a digital signal, and the resulting N sample value (digital signal for 1 echo) is temporarily stored in the sample memory itself. A stop signal is meanwhile sent to the timing circuit 15, and the timing is stopped. Subsequently, when there is a transmission command from the CPU 11, the N sample values stored in the sampling memory are sequentially transmitted to the CPU 11. The CPU 11 sequentially takes in the N sample values from the A/D convertor 8 and stores the current echo waveform in the waveform memory area of RAM 10, the maximum value among the N sample values is extracted to detect the current echo level (current echo amplitude), and the detected results are stored in the echo data memory area of RAM 10 (step SQ14). Meanwhile, the echo arrival time is read from the timing circuit 15 when the echo signal is read in, and the current echo arrival time thus read in is stored in the data memory area of the RAM 10. The current echo level stored in RAM 10, as shown by the broken line in FIG. 4, is displayed by the deflection of the liquid crystal needle pattern 12a in the level meter 12 (step SQ15).

The CPU 11 then reads out the current echo level and the maximum echo level from the echo data memory area of RAM 10 to determine whether or not the current echo level value is greater than the maximum echo level value (step SQ16). This is the first determination, and since the maximum echo level value is the initialized value "0," the CPU 11 determines that the current echo level value is greater than the maximum echo level value, the maximum echo level value stored in the echo data memory area of RAM 10 is replaced by the current echo level value, the maximum echo arrival time corresponding to the maximum echo level is replaced by the current echo arrival time, and the maximum echo waveform stored in the waveform memory area of RAM 10 is also replaced by the current echo waveform (step SQ17).

The new maximum echo waveform is displayed on the screen of the display 13, and the new maximum echo level is displayed by the deflection of the liquid crystal needle pattern 12b on the level meter 12, as shown by the solid line in FIG. 4 (step SQ18). Then, when the CPU 11 looks for the measurement continue flag in RAM 10 (step SQ19) and raises the measurement continue flag (when the contents of the measurement flag are "1"), the CPU 11 determines that measurement is to continue, repeats the 1 pulse emission and 1 echo reception described above (steps SQ12 through SQ15), and then again reads out the current echo level and maximum echo level from the echo data memory area in RAM 10 in step SQ16 to determine whether or not the current echo level value is greater than the value of the maximum echo level. When it is determined that the current echo level is not greater than the maximum echo level, the system jumps directly to step SQ19 without modifying the values, and looks for the measurement continue flag.

As long as the operator does not press the measurement end switch, the contents of the measurement continue flag are "1," and the CPU 11 repeats the 1 pulse emission 1 echo transmission described above (steps SQ12 through QP15) and the maximum echo level extraction (steps SQ16 through SQ19). While the CPU 11 is repeating the process described above (steps SQ12 through SQ19), the operator aims the transducer 1 at the skin surface X, as indicated by the arrow W in FIG. 4, and changes the direction and angle of the transducer 1 by sometimes describing a circle or spiral in the manner of the precession of a top and sometimes oscillating it in any direction in the manner of a seesaw on the cortical bone Mb at the measuring site while checking the direction in which the liquid crystal needle patterns 12a and 12b of the level meter 12 oscillate the greatest, that is, the direction in which the maximum echo level is detected. As described in the first embodiment, echoes Ae reflected roughly perpendicularly at the surface Y of the cortical bone Mb can be considered to have returned to the transducer surface of the transducer 1 when the echo level is greatest. Thus, the echo arrival time Ta during the maximum level measured at this time is the time the echo $An_2$ perpendicularly reflected at the surface Y of the cortical bone Mb takes to return to the transducer surface of the transducer 1 after the ultrasonic pulse Ai has been emitted. The liquid crystal patterns 12a and 12b of the level meter 12 change in a sensitive manner (oscillate vigorously) in the event of pronounced nonalignment between the normal of the cortical bone Mb and the normal of the transducer surface, but since such changes are blunted (the oscillation abates) when the normals are roughly aligned, it is relatively easy to find a perpendicularly reflected echo Ae.

When the operator looks at the extent of oscillation in the liquid crystal needle patterns 12a and 12b of the level meter and determines that the maximum echo level can be extracted, the measurement end switch is pressed. When the measurement end switch is pressed, the CPU 11 rewrites the contents of the measurement continue flag as "0" by an interrupt process so as to lower the measurement continue flag. When the measurement continue flag is lowered, the CPU 11 stops any subsequent 1 pulse emissions (step SQ19). The maximum echo level stored in the echo data memory area of RAM 10 is read out and displayed on the screen of the display 13 (step SQ20).

The CPU 11 then moves to a high speed Fourier transform routine, reads out the maximum echo waveform ve(t) from the waveform memory area in RAM 10 for Fourier transformation, and determines the maximum echo waveform spectrum (hereinafter referred to as maximum echo spectrum). The maximum echo spectrum Ve($\omega$) is converted to a frequency f, for example, to determine the frequency components within a range from about 300 kHz to 2.5 MHz. The complex reflection coefficient calculating routine is then executed so as to calculate the ultrasonic complex reflection coefficient R($\omega$) (step SQ21) at the interface between the soft tissue Ma and cortical bone Mb of the patient at an angular frequency $\omega$ based on the maximum echo spectrum Ve($\omega$) thus calculated, and the calculated value is displayed on the screen of the display 13 (step SQ22).

In step SQ21, the ultrasonic complex reflection coefficient R($\omega$) is given by Formula (29).

$$R(\omega) = \frac{Ru(\omega)Ve(\omega)e^{-j\omega(Ta-Tu)}}{Vu(\omega)} \quad (29)$$

j: imaginary unit

Ve($\omega$): maximum echo spectrum for echo Ae perpendicularly reflected at surface Y of cortical bone Mb Ta: echo arrival time during maximum level of echo Ae perpendicularly reflected at surface Y of Cortical bone Mb Vu($\omega$): maximum echo spectrum (known) of echo perpendicularly reflected at pseudo-cortical bone Tu: echo arrival time (known) during maximum level of echo perpendicularly reflected at pseudo-cortical bone Ru($\omega$): ultrasonic complex reflection coefficient (known) of pseudo-cortical bone relative to pseudo-soft tissue Ma at angular frequency $\omega$ Here, exp $\{-j\omega(Ta-Tu)\}$ is a factor expressing the phase difference between an echo Ae from the surface Y of the cortical bone Mb and an echo Au from the surface of the pseudo-cortical bone, which are each received at the transducer surface of the transducer 1, and is intended to compensate for the difference between the thickness of the soft tissue Ma of the patient and the standard thickness of pseudo-soft tissue during the measurement of the pseudo-cortical bone.

A substance having acoustic properties similar to those of cortical bone Mb (in this case, an acrylic resin) may be used as the pseudo-cortical bone. A substance having acoustic properties similar to those of soft tissue Ma (in this case, water) may be used as the pseudo-soft tissue placed directly in front of the pseudo-cortical bone. The values for the maximum echo spectrum Vu($\omega$) for pseudo-cortical bone and echo arrival time Tu during the maximum level are obtained by previously introducing an acrylic resin block (pseudo-cortical bone) having a known ultrasonic complex reflection coefficient Ru($\omega$) in a water tank (pseudo-soft tissue), arranging the transducer 1 at a distance corresponding to the standard thickness of the soft tissue Ma with respect to the block, emitting ultrasonic pulses Ai at the pseudo-cortical bone, and effecting the Fourier transform process described above or the like on the echo data thus obtained. The resulting values for the maximum echo spectrum Vu($\omega$) for pseudo-cortical bone and echo arrival time Tu during the maximum level are stored in ROM 9 along with the known ultrasonic complex reflection coefficient Ru($\omega$).

The CPU 11 then executes the complex acoustic impedance calculating routine so as to calculate the complex acoustic impedance Zb($\omega$) for cortical bone Mb by substituting the ultrasonic complex reflection coefficient R($\omega$) given by the complex reflection coefficient calculating routine into Formula (27) (step SQ23).

When the patient's osteoporosis is advanced, resulting in [|Za($\omega$)|>|Zb($\omega$)|], the real part of R($\omega$), from Formula (28), is negative. This means that the phase of echo Ae is inverted at the surface Y of the cortical bone Mb. The CPU 11 displays the calculated results of the complex acoustic impedance Zb($\omega$) for cortical bone Mb on the screen of the display 13 (step SQ 24).

The acoustic impedance of bone is given by the square root of [elastic modulus×density] of bone, and the elastic modulus of bone increases (or decreases) with increases (or decreases) in bone density, so the elastic modulus of bone and bone density play a synergistic role in acoustic impedance. Thus, because the acoustic impedance serves as an index of osteoporosis in the structure of this embodiment, it is capable of sensitive response to the extent to which osteoporosis has progressed. For example, when the acoustic impedance of cortical bone is far lower than the mean value for a given age level, the osteoporosis of the cortical bone can be considered to have deteriorated.

Furthermore, from Formula (29), phase data can be determined along with the magnitude of the ultrasonic complex reflection coefficient R($\omega$), so the diagnosis will not be erroneous even when the acoustic impedance of cortical bone is lower than the acoustic impedance for soft tissue. In contrast, in methods where the reflection coefficient R is not given in the form of complex numbers, the diagnosis is sometimes erroneous because in such cases the CPU 11 takes an absolute value |R| for the ultrasonic reflection coefficient R in calculations using [Zb=Za (1+|R|)/(1−|R|)= Za (1−R)/(1+R) ] (Formula (5)).

Embodiment 9

Figure 13:
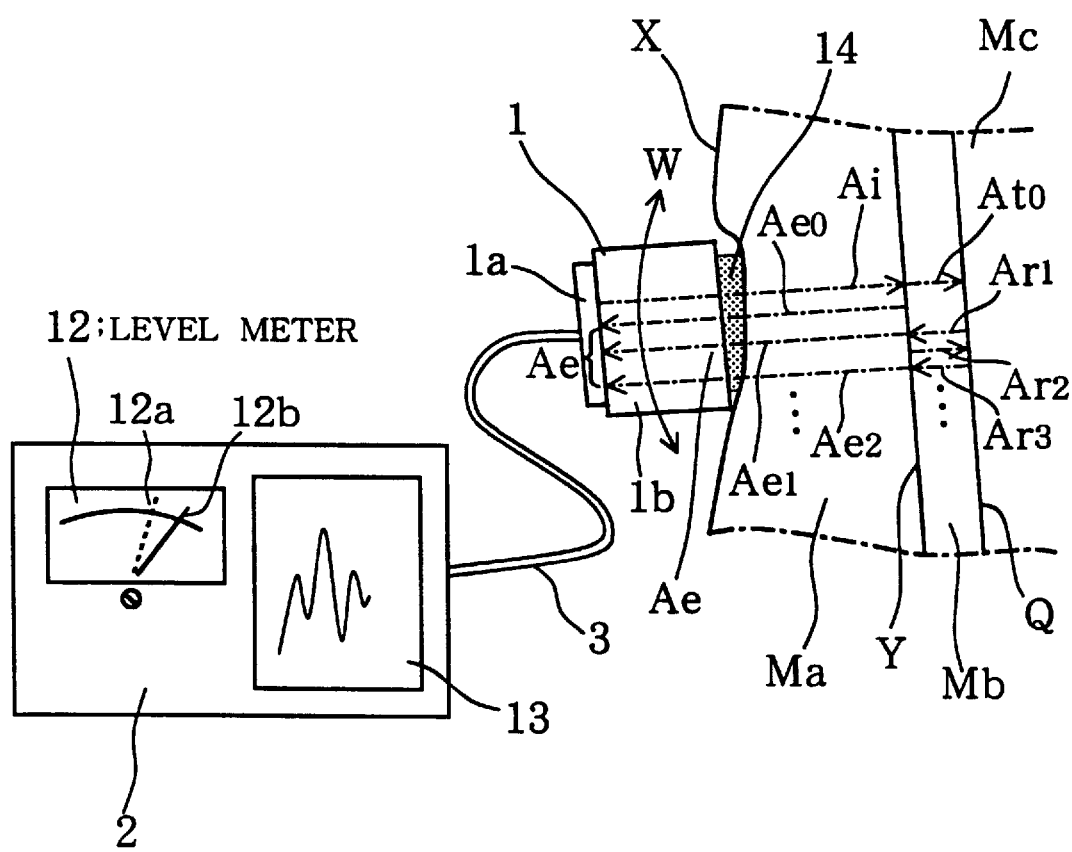
FIG. 13 schematically depicts the apparatus for diagnosing osteoporosis while in use in a ninth embodiment of the present invention.
Figure 14:
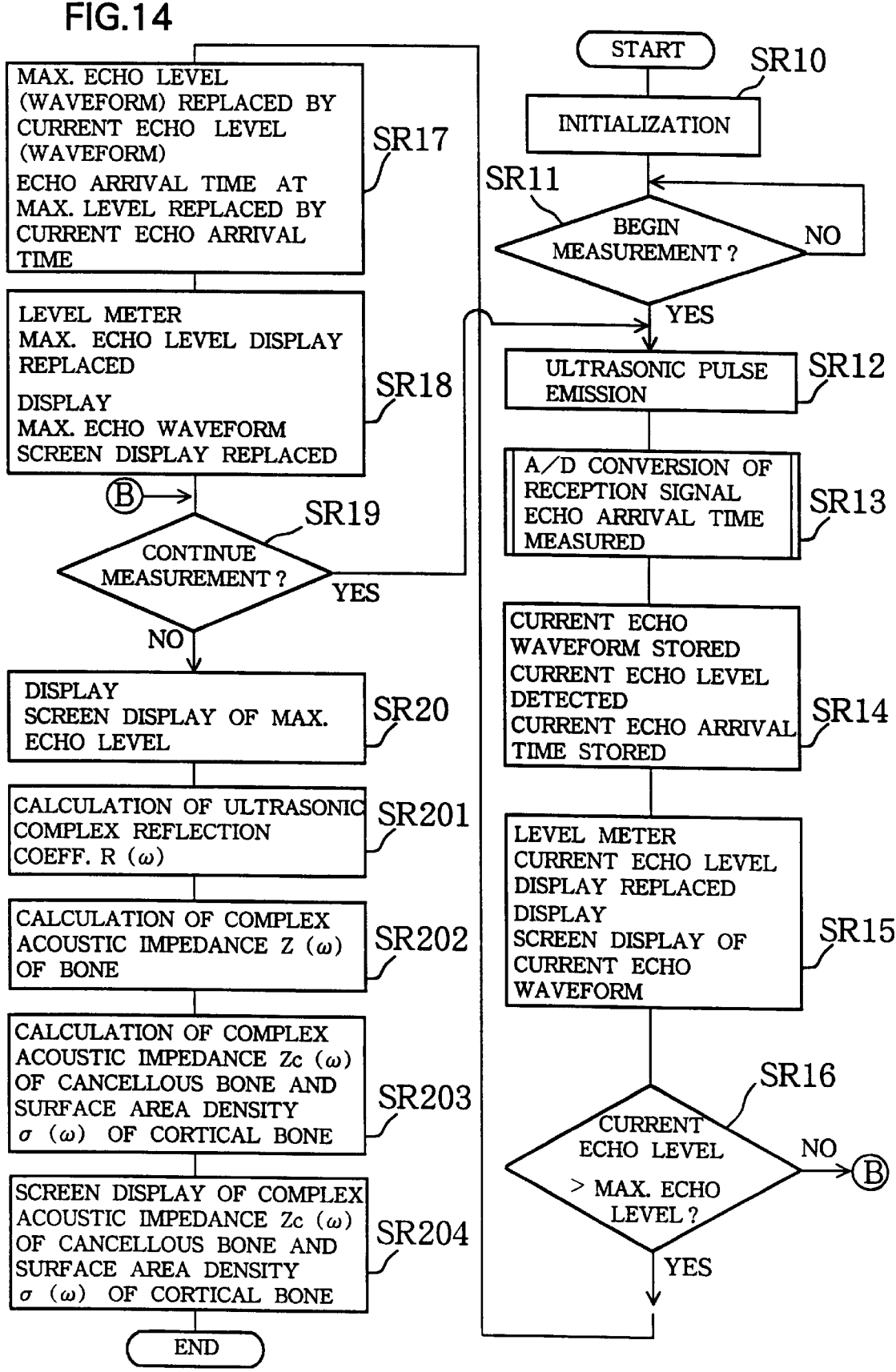
FIG. 14 is a flow chart of the operation and processing procedures of the same apparatus.

FIG. 13 schematically depicts the apparatus for diagnosing osteoporosis while in use in a ninth embodiment of the present invention, and FIG. 14 is a flow chart of the operation and processing procedures of the same apparatus.

The complex acoustic impedance could not be calculated unless the cortical bone was of a certain thickness in the apparatus for diagnosing osteoporosis in the eighth embodiment, whereas a feature of the apparatus for diagnosing osteoporosis in this example is that even thin cortical bone (such as the thin heel bone, which is immediately adjacent to cancellous bone Mc on the side opposite the soft tissue Ma) can be selected as a measuring site.

Echoes produced in cortical bone that is not thick are different from those produced in cortical bone of a certain thickness. In cortical bone that is not thick, as shown in FIG. 13, a portion of the ultrasonic pulse Ai emitted at the cortical bone Mb is reflected at a reflection coefficient Sb at the surface Y, resulting in echo Ae0, and a portion passes through at a transmission coefficient Tb in the form of a transmission ultrasonic wave At0, penetrating the cortical bone Mb and arriving at the interface Q with cancellous bone Mc. At the interface Q with the cancellous bone Mc, a portion of the transmission ultrasonic wave At0 is reflected at a reflection coefficient Sc, resulting in a reflected ultrasonic wave Ar1, and returns through the cortical bone Mb. A portion of the reflected ultrasonic wave Ar1 passes through the interface Y with soft tissue Ma at a transmission coefficient Tb, resulting in an echo Ae1 toward the transducer 1, and a portion is reflected at the interface Y with the soft tissue Ma, resulting in a reflected ultrasonic wave Ar2, and arrives back at the interface Q with the cancellous bone Mc. A portion of the reflected ultrasonic wave Ar2 is reflected here again, resulting in a reflected ultrasonic wave Ar3, and returns through the cortical bone Mb, and a portion passes through the interface Y with the soft tissue Ma at a transmission coefficient Tb, resulting in an echo Ae1 toward the transducer 1. Accordingly, the echo Ae returning from the cortical bone Mb involves an overlapping of echoes Ae0, Ae1, Ae2, etc. which are obtained in the course of the multiple reflections described above. The ultrasonic complex reflection coefficient $R(\omega)$ of the patient's bone is thus given by Formula (30).

$$R(\omega) = Sb(\omega) + \frac{Tb^2(\omega)Sc(\omega)e^{-2j\omega\tau}}{1 + Sb(\omega)Sc(\omega)e^{-2j\omega\tau}} \qquad (30)$$

$\tau$: time for ultrasonic wave to propagate through cortical bone Mb of a thickness L In the case of perpendicular incidence, Formulas (31) and (32) are used for the interface Y between cortical bone Mb and soft tissue Ma, and Formula (33) is used for the interface Q between the cancellous bone Mc and cortical bone Mb.

$$Sb(\omega) = \{Zb(\omega) - Za(\omega)\}/\{Zb(\omega) + Za(\omega)\} \qquad (31)$$

$$Tb(\omega) = 2\{Zb(\omega)Za(\omega)\}^{1/2}/\{Zb(\omega) + Za(\omega)\} \qquad (32)$$

$$Sc(\omega) = \{Zc(\omega) - Zb(\omega)\}/\{Zc(\omega) + Zb(\omega)\} \qquad (33)$$

Zc: complex acoustic impedance for cancellous bone Mc

Formulas (31), (32), and (33) are each substituted into Formula (30), and are arranged when the thickness L of the cortical bone Mb is sufficiently smaller than the ultrasonic wavelength to obtain Formula (34) giving the complex acoustic impedance $Z(\omega)$ which takes into account the multiple echoes Ae0, Ae1, Ae2, etc.

$$Z(\omega) = Zc(\omega) + \frac{j\omega\tau[Zb^2(\omega) - Zc^2(\omega)]}{Zb(\omega)} \qquad (34)$$

As shown in Formula (35), Formula (34) is simplified when taking into account $Zb(\omega) \gg Zc(\omega)$.

$$Z(\omega) = Zc(\omega) + j\omega\tau Zb(\omega) = Zc(\omega) + j\omega\rho L \qquad (35)$$

$\rho$: bone density of cortical bone Mb

Here, $\rho L$ is the mass per unit surface area of cortical bone Mb, that is, the area density $\sigma$.

Although the complex acoustic impedance $Z(\omega)$ of bone can be calculated on the basis of echo data in conformance with Formula (27), the real and imaginary parts of Formulas (27) and (35) are equal, so the complex acoustic impedance $Zc(\omega)$ of cancellous bone Mc can be determined from the real parts, and the area density $\sigma$ of the cortical bone Mb can be determined from the imaginary parts. In this case, the bone density $\rho$ of the cortical bone Mb can be determined if the thickness L of the cortical bone Mb is known. The processing program in this example includes Formula (35) and the like, and takes into account the multiple echoes Ae0, Ae1, Ae2, etc.

The operation of this example (primarily the CPU 11 processing during the diagnosis of osteoporosis) is described below with reference to FIG. 14.

Steps SR10 to SR20 in the processing in this example are roughly the same as those in the eighth embodiment (steps SQ10 to SQ20 (FIG. 12)), so the description here will begin with step SR20 for the sake of convenience.

The CPU 11 displays the maximum echo level on the screen of the display 13 (step SR20), and then advances to step SR201 and executes the high speed Fourier transform routine, so as read out the maximum echo waveform ve(t) from the waveform memory area of RAM 10 for Fourier transformation and determine the maximum echo spectrum $Ve(\omega)$. The complex reflection coefficient calculating routine is then executed so as to calculate the ultrasonic complex reflection coefficient $R(\omega)$ at the interface between the patient's soft tissue Ma and bone at an angular frequency $\omega$ on the basis of the maximum echo spectrum $Ve(\omega)$ thus calculated. The ultrasonic complex reflection coefficient $R(\omega)$ in this example is derived by means of Formula (29), in the same manner as in the eighth embodiment, using the maximum echo spectrum $Ve(\omega)$ and echo arrival time Ta during the maximum level for the patient's bone, as well as the maximum echo spectrum $Vu(\omega)$, echo arrival time Tu during the maximum level, and the ultrasonic complex reflection coefficient $Ru(\omega)$ for pseudo-cortical bone.

The maximum echo spectrum $Vu(\omega)$ and the echo arrival time Tu during the maximum level for pseudo-cortical bone were determined for pseudo-cortical bone of known ultrasonic complex reflection coefficient $Ru(\omega)$ by roughly the same procedure as that when the maximum echo waveform and echo arrival time during the maximum level were determined for pseudo-cortical bone in the eighth embodiment, and were stored along with the known ultrasonic complex reflection coefficient $Ru(\omega)$ in ROM 9. In this example, however, the maximum echo spectrum $Vu(\omega)$ and echo arrival time Tu during the maximum level for pseudo-cortical bone were obtained by first immersing pseudo-cancellous bone consisting of a substance having acoustic properties similar to those of cancellous bone Mc in a water tank filled with water or the like, placing pseudo-cortical bone of a predetermined thickness on the pseudo-cancellous bone, then arranging the transducer 1 at a distance corresponding to a standard thickness of soft tissue Ma with respect to the pseudo-cortical bone, emitting an ultrasonic pulse Ai at the pseudo-cortical bone, and executing the Fourier transform process or the like described above on the echo data thus obtained. The CPU 11 then moves to the complex acoustic impedance calculating routine, and the ultrasonic complex reflection coefficient $R(\omega)$ thus calculated is substituted into Formula (27) to determine the complex acoustic impedance $Z(\omega)$ for the patient's bone (step SR202). The CPU 11 then determines the complex acoustic impedance $Zc(\omega)$ for the patient's cancellous bone and the area density $\sigma$ of the cortical bone Mb from the resulting complex acoustic impedance $Z(\omega)$ for bone and Formula (35)(step SR203), and displays them on the screen of the display 13 (step SR204).

The structure of the ninth embodiment allows data such as the area density $\sigma$ to be obtained even when the cortical bone Mb is thinner than the ultrasonic wavelength. In this case, the bone density $\rho$ of the cortical bone Mb can also be learned when the thickness L of the patient's cortical bone Mb is known. The complex acoustic impedance Zc for cancellous bone Mc can also be learned.

Embodiment 10

Figure 15:
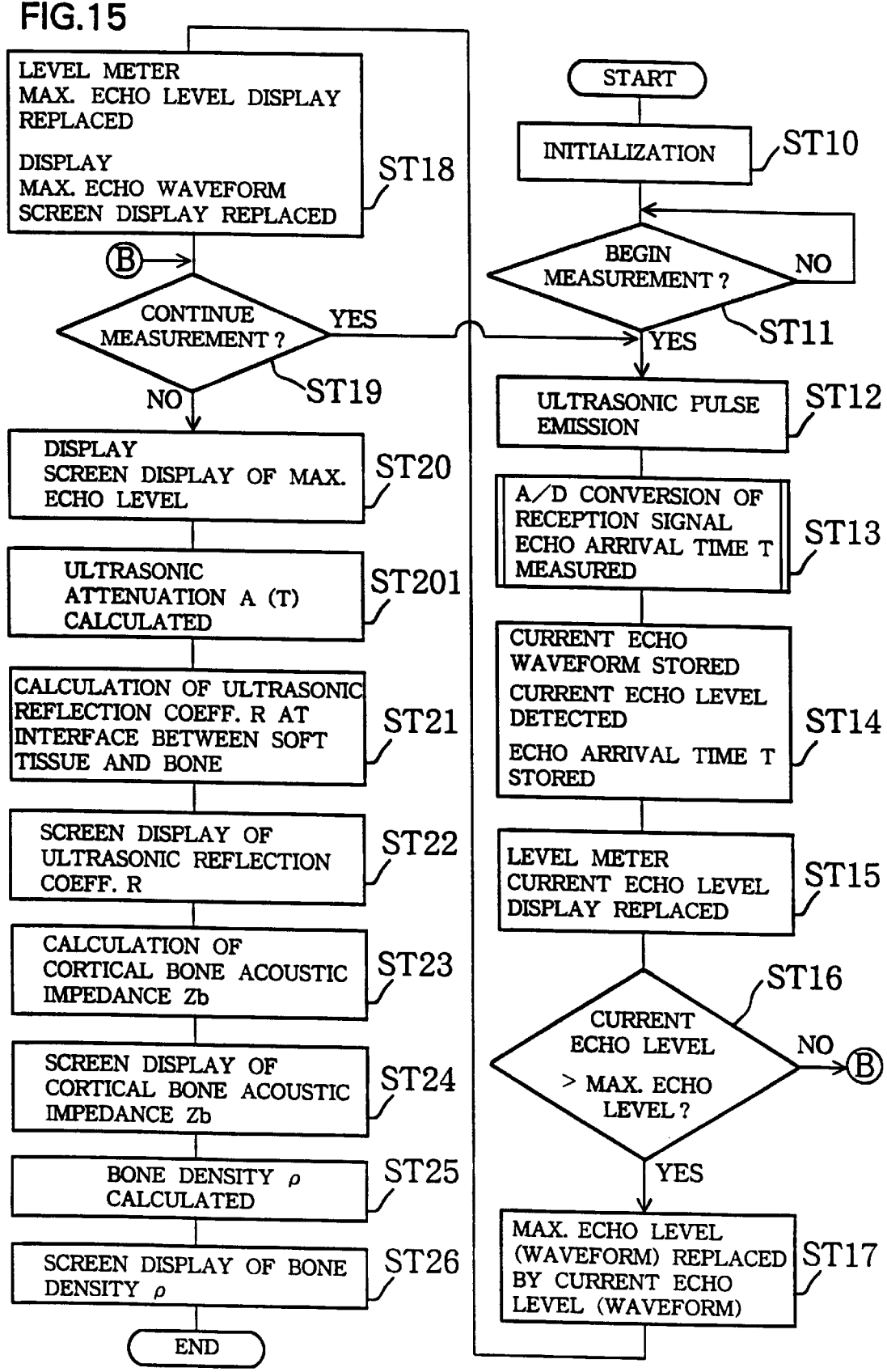
FIG. 15 is a flow chart of the operation and processing procedures of the apparatus for diagnosing osteoporosis in a tenth embodiment of the present invention.

FIG. 15 is a flow chart of the operation and processing procedures of the apparatus for diagnosing osteoporosis in a tenth embodiment of the present invention.

The hardware in the tenth embodiment has roughly the same structure as that in the eighth embodiment, so the structure in this example will be described with reference to FIG. 11. In the structure of the apparatus for diagnosing osteoporosis in this example, the attenuation A(T) during the reciprocal movement of the ultrasonic wave through soft tissue Ma is taken into account, allowing the acoustic impedance Zb for cortical bone Mb to be measured with even greater accuracy. The apparatus main unit 2*a* in this example has a timing circuit 14 for measuring the echo arrival time T from after the emission of the ultrasonic impulse Ai from the transducer surface of the transducer 1 until the echo Ae returns to the transducer surface. The processing program in this example includes a procedure in which the ultrasonic reflection coefficient R for cortical bone Mb relative to the soft tissue Ma of the patient is calculated on the basis of the maximum echo level and the echo arrival time T at this time.

The operation of this example (primarily the processing of the CPU 11 during the diagnosis of osteoporosis) is described below with reference to FIG. 15.

After the CPU 11 has sent a 1 pulse generating command to the pulse generator 4 (step ST12), it issues a sampling start command (step SP13) to the A/D convertor 8 upon measuring the time in which the transmission resonance $An_1$ is received by the ultrasonic oscillator 1a of the transducer 1, the echo $An_2$ from the skin is then received, and the echo Ae from the cortical bone Mb returns to the transducer surface of the oscillator 1a of the transducer 1. In step ST14, the CPU 11 then reads the echo waveform (echo signal) from the A/D convertor 8a, reads the echo arrival time T from the timing circuit 14, and stores the current echo waveform (current echo signal) and echo arrival time T thus read in the echo data memory area of RAM 10. After the conclusion of the measurement (steps ST19 and ST20), the CPU 11 first moves to the ultrasonic attenuation calculating routine to read RAM 10, and substitutes the echo arrival time Tsec into Formula (36) to calculate the ultrasonic attenuation A(T) in the patient's soft tissue Ma (step ST201).

$$A(T) = 10^{\frac{-1.1T}{20 \cdot 0.01/1500}} \tag{36}$$

Here, the attenuation A(T) means the level of attenuation during the reciprocal movement of the ultrasonic waves in soft tissue Ma, that is, the attenuation when the ultrasonic waves are propagated from the surface X of the skin to the surface Y of the of the cortical bone Mb and are reflected at the surface Y of the cortical bone Mb back again to the surface X of the skin (the lower the A(T), the greater the attenuation). The attenuation A(T) is a function of the echo arrival time T, the relation of which is determined by experiment or simulation.

Ultrasonic waves undergo attenuation in the soft tissue Ma because, first, the ultrasonic waves used in this example are not completely flat, but also contain multiple spherical wave components, resulting in the scattering of acoustic energy (ultrasonic scattering), and second, because acoustic energy is converted to thermal energy (ultrasonic absorption) by friction with the soft tissue Ma. The extent of attenuation caused by ultrasonic scattering can be determined by measurement or experiment from the aperture of the transducer 1, ultrasonic frequency, acoustic velocity of soft tissue Ma, and the like.

The extent of attenuation caused by ultrasonic absorption is lower when the ultrasonic frequency is lower, and an absorption constant typical of soft tissue Ma (ultrasonic attenuation rate per unit length) can be used even when the frequency is not sufficiently low. Formula (36) giving the ultrasonic attenuation A(T) is an empirical formula that is obtained when the central ultrasonic frequency used is set at 2.5 MHz, and the aperture of the transducer 1 is set at 15 mm.

The CPU 11 then reads the maximum echo level Ve from the echo data memory area of RAM 10 and substitutes it along with the calculated attenuation A(T) into Formula (37) to calculate the ultrasonic reflection coefficient R at the interface between soft tissue Ma and cortical bone Mb when the ultrasonic waves land perpendicular on the cortical bone Mb from the soft tissue Ma (step ST21).

$$R = Ve/P \cdot Q \cdot B \cdot Vi \cdot A(T) \tag{37}$$

Here, P, Q, B, and Vi mean the same as in Formula (10). Formula (37) is derived in the following manner. First, when an electrical signal of amplitude Vi is applied from the pulse generator 4 to the transducer 1, an ultrasonic impulse Ai of a sound pressure PVi is introduced from the transducer surface of the transducer 1 into the soft tissue Ma. As the ultrasonic impulse Ai thus introduced is attenuated during its propagation in the soft tissue Ma (assuming it lands perpendicular to the surface Y of the cortical bone Mb), it is reflected perpendicularly at the surface Y of the cortical bone Mb, resulting in echo Ae, and returns perpendicular to the transducer 1. The sound pressure P(e) of the echo Ae returning to the transducer surface of the transducer 1 is thus given by Formula (38), taking into account the attenuation A(T) during the reciprocal movement of the ultrasonic waves in soft tissue Ma determined from Formula (36).

$$P(e) = P \cdot Vi \cdot R \cdot A(T) \tag{38}$$

When an echo Ae having a sound pressure P(e) is received at the transducer surface of the transducer 1, the transducer 1 outputs a reception signal having an amplitude Q·P(e), and this reception signal is amplified at an amplitude B by the amplifier 6 (and waveform shaper 7). Following digital conversion by the A/D convertor 8a, the signal is taken in by the CPU 11 and detected in the form of the maximum echo level Ve (=B·Q·P(e)). The maximum echo level Ve is thus given by Formula (39).

$$Ve = P \cdot Vi \cdot R \cdot A(T) \cdot B \cdot Q \tag{39}$$

Formula (37) is obtained when Formula (39) is solved for the ultrasonic reflection coefficient R. To return to the description of the flow chart in FIG. 15, the CPU 11 calculates the ultrasonic reflection coefficient R at the interface between soft tissue Ma and cortical bone Mb using Formula (37) (step ST21), and displays the calculated results on the screen of the display 13 (step ST22). The CPU 11 calculates the acoustic impedance Zb for the patient's cortical bone Mb using Formula (5) (step ST23), and displays the calculated results on the screen of the display 13 (step ST24).

Subsequently, the bone density of the patient's cortical bone Mb (density of cortical bone) ρ is calculated (step ST25) on the basis of the calculated value of the acoustic impedance Zb by the same means as in the first through seventh embodiments described above, and the calculated results are displayed on the screen of the display 13 (step ST26).

In the structure described above, the attenuation A(T) during the reciprocal movement of the ultrasonic waves in soft tissue Ma is taken into consideration in addition to the effects of the first embodiment described above, allowing the acoustic impedance Zb of cortical bone Mb and the bone density ρ of cortical bone Mb to be measured with even greater accuracy.

Embodiments of the present invention were described in detail above with reference to figures, but the specific structure is not limited to these embodiments, and the present invention includes modifications in design and the like which are within the essential scope of the present invention. For example, the bone serving as the measuring site is not limited to cortical bone such as the tibia, the top of the patella, or the heel, as long as it can be considered flat. The ultrasonic oscillator constituting the transducer is not limited to a thickness oscillation type and may be a flexural oscillation type.

Since the acoustic impedance of soft tissue Ma is close to the acoustic impedance of $1.5 \times 10^6$ kg/m²sec for water, the acoustic impedance for water may be used instead of that for soft tissue Ma to calculate the ultrasonic reflection coefficient using Formula (31). The various processing programs of the CPU 11 may be stored in an external memory device such as a hard disk as needed instead of being stored in ROM 9. Part or all of the structural components of the apparatus for diagnosing osteoporosis in the present invention may be hardware structures and software structures.

The method for calculating the ultrasonic reflection coefficient R is not limited to the methods described in the embodiments above. For example, when one end surface of the transducer 1 is a free end and echoes are measured from one end surface, the ultrasonic waves are completely reflected at one end surface, so the reflection level at this time is equivalent to the incident wave level. As such, the ultrasonic reflection coefficient R can be determined as the ratio between the incident wave level and the echo level from the cortical bone Mb.

In the first embodiment described above, the regression coefficient a used in the recurrence formula for calculating bone density was $1.80 \times 10^{-4}$, but, as is apparent in the third embodiment, the regression coefficient $\alpha$ should range from $1.27 \times 10^{-4}$ to $2.34 \times 10^{-4}$. Similarly, the section $\beta$ is constant at 766, but may range from 646 to 887. In the fourth embodiment described above, the regression coefficient A used in the recurrence formula for calculating bone density was 0.342, but, as is apparent in the fifth embodiment, the regression coefficient A should range from 0.239 to 0.445. Similarly, the constant B was constant at $10^{0.894}$, but may range from $10^{0.239}$ to $10^{1.55}$. In the sixth embodiment described above, the regression coefficient $\alpha'$ used in the recurrence formula for calculating bone density was 843, but, as is apparent in the seventh embodiment, it may range form 588 to 1100. Similarly, the section $\beta'$ was constant at 1000, but may range from 953 to 1060.

In the fourth embodiment described above, a nonlinear recurrence formula (Formula (15)) for bone density ρ relative to acoustic impedance Zb was used, but as indicated in Formula (40), a nonlinear recurrence formula for the density of cortical bone relative to ultrasonic reflection coefficient can similarly be used.

$$\rho = B'R^{A'} \tag{40}$$

ρ: cortical bone density [kg/m³]
R: ultrasonic reflection coefficient at interface between soft tissue and cortical bone of patient
A': regression index
B': constant [sec/m]

INDUSTRIAL APPLICABILITY

The ultrasonic reflection type of apparatus and method for diagnosing osteoporosis in the present invention are suitable for use in hospitals, sports facilities, health care facilities, and the like, but since the apparatus is compact and lightweight, is easy to operate, and is free of the danger of radiation exposure, it is particularly desirable for use as a household health management instrument for the elderly.

What is claimed is:

1. An ultrasonic reflection type of apparatus for diagnosing osteoporosis having an ultrasonic transducer for transmitting and receiving ultrasonic pulses, wherein the ultrasonic pulses are repeatedly radiated toward cortical bone in a subject, the echoes reflected on the surface of the cortical bone at that time are received, the density of the subject's cortical bone is calculated based on the resulting echo data, and osteoporosis is diagnosed based on cortical bone density thus calculated, said apparatus for diagnosing osteoporosis comprising:

echo level detecting means for detecting the echo level of the echoes reflected on the surface of the cortical bone when the ultrasonic pulses are radiated;

maximum echo level extracting means for extracting the maximum echo level from among the echo levels thus detected;

reflection coefficient calculating means for calculating the ultrasonic reflection coefficient at the interface between the soft tissue and cortical bone of the subject based on the extracted maximum echo level; and bone density calculating means for calculating the density of the subject's cortical bone using a predetermined recurrence formula for said cortical bone density relative to said ultrasonic reflection coefficient.

2. An ultrasonic reflection type of apparatus for diagnosing osteoporosis having an ultrasonic transducer for transmitting and receiving ultrasonic pulses, wherein the ultrasonic pulses are repeatedly radiated toward cortical bone in a subject, the echoes reflected on the surface of the cortical bone at that time are received, the density of the subject's cortical bone is calculated based on the resulting echo data, and osteoporosis is diagnosed based on cortical bone density thus calculated, said apparatus for diagnosing osteoporosis comprising:

echo level detecting means for detecting the echo level of the echoes reflected on the surface of the cortical bone when the ultrasonic pulses are radiated;

maximum echo level extracting means for extracting the maximum echo level from among said echo levels;

acoustic impedance calculating means for calculating the acoustic impedance of the subject's cortical bone based on the extracted maximum echo level; and bone density calculating means for calculating the density of the subject's cortical bone using a predetermined recurrence formula for said cortical bone density relative to said acoustic impedance.

3. An apparatus for diagnosing osteoporosis as defined in claim 2, wherein said acoustic impedance calculating means calculates the ultrasonic reflection coefficient of the cortical bone relative to the soft tissue of the subject based on the maximum echo level extracted by the maximum echo level extracting means, and then calculates said acoustic impedance of the subject's cortical bone based on ultrasonic reflection coefficient thus calculated.

4. An ultrasonic reflection type of apparatus for diagnosing osteoporosis having an ultrasonic transducer for transmitting and receiving ultrasonic pulses, wherein the ultrasonic pulses are repeatedly radiated toward cortical bone in a subject, the echoes reflected on the surface of the cortical bone at that time are received, the density of the subject's cortical bone is calculated based on the resulting echo data, and osteoporosis is diagnosed based on cortical bone density thus calculated, said apparatus for diagnosing osteoporosis comprising:

echo level detecting means for detecting the echo level of the echoes reflected on the surface of the cortical bone when the ultrasonic pulses are radiated;

a maximum echo level extracting program containing the processing procedure for extracting the maximum echo level from among the echo levels thus detected;

a reflection coefficient calculating program containing the processing procedure for calculating the ultrasonic reflection coefficient at the interface between the soft tissue and cortical bone of the subject based on maximum echo level that has been extracted;

a bone density calculating program containing the processing procedure for calculating the density of the subject's cortical bone using a predetermined recurrence formula for said cortical bone density relative to said ultrasonic reflection coefficient;

a first memory for storing various processing programs, including the maximum echo level extracting program, reflection coefficient calculating program, and bone density calculating program;

a second memory for temporarily storing data, including the echo levels thus detected and maximum echo levels that have been extracted; and a central processing unit for calculating the density of the subjects' cortical bone by using said second memory to execute the various programs stored in said first memory.

5. An ultrasonic reflection type of apparatus for diagnosing osteoporosis having an ultrasonic transducer for transmitting and receiving ultrasonic pulses, wherein the ultrasonic pulses are repeatedly radiated toward cortical bone in a subject, the echoes reflected on the surface of the cortical bone at that time are received, the density of the subject's cortical bone is calculated based on the resulting echo data, and osteoporosis is diagnosed based on cortical bone density thus calculated, said apparatus for diagnosing osteoporosis comprising:

echo level detecting means for detecting the echo level of the echoes reflected on the surface of the cortical bone when the ultrasonic pulses are radiated;

a maximum echo level extracting program containing the processing procedure for extracting the maximum echo level from among the echo levels thus detected;

an acoustic impedance calculating program containing the processing procedure for calculating the acoustic impedance of the subject's cortical bone based on maximum echo level that has been extracted;

a bone density calculating program containing the processing procedure for calculating the density of the subject's cortical bone using a predetermined recurrence formula for said cortical bone density relative to said acoustic impedance;

a first memory for storing various processing programs, including the maximum echo level extracting program, reflection coefficient calculating program, acoustic impedance calculating program, and bone density calculating program;

a second memory for temporarily storing data, including the detected echo levels and extracted maximum echo levels; and a central processing unit for calculating the density of the subjects' cortical bone by using said second memory to execute the various programs stored in said first memory.

6. An apparatus for diagnosing osteoporosis as defined in claim 5, wherein said acoustic impedance calculating program contains the processing procedure for calculating said ultrasonic reflection coefficient of the cortical bone relative to the soft tissue of the subject based on said maximum echo level extracted by said maximum echo level extracting means, and the processing procedure for calculating said acoustic impedance of the subject's cortical bone based on ultrasonic reflection coefficient thus calculated.

7. An apparatus for diagnosing osteoporosis as defined in claim 1 or claim 4, wherein said recurrence formula for said cortical bone density relative to said ultrasonic reflection coefficient is given in the form of the following formula.

$$\rho = \alpha' R + \beta'$$

$\rho$: density of cortical bone [kg/m$^3$]
R: ultrasonic reflection coefficient at interface between soft tissue and cortical bone of subject
$\alpha'$: regression coefficient [kg/m$^3$]
$\beta'$: section [kg/m$^3$]

8. An apparatus for diagnosing osteoporosis as defined in claim 7, wherein aid regression coefficient $\alpha'$ is established within the range of 588 to 1100.

9. An apparatus for diagnosing osteoporosis as defined in claim 7, wherein said section $\beta'$ is established within the range of 953 to 1060.

10. An apparatus for diagnosing osteoporosis as defined in claim 1 or claim 4, wherein said recurrence formula for said cortical bone density relative to said ultrasonic reflection coefficient is given in the form of the following formula.

$$\rho = B' R^{A'}$$

$\rho$: density of cortical bone [kg/m$^3$]
R: ultrasonic reflection coefficient at interface between soft tissue and cortical bone of subject
A': regression coefficient
B': constant [sec/m]

11. An apparatus for diagnosing osteoporosis as defined in claim 3 or claim 6, wherein said acoustic impedance of the subject's cortical bone is given by the following formula, $$Zb = Za(R+1)/(1-R)$$

Zb: acoustic impedance of cortical bone in subject
Za: acoustic impedance of soft tissue or acoustic impedance of water
R: ultrasonic reflection coefficient at interface between soft tissue and cortical bone of subject 12. An apparatus for diagnosing osteoporosis as defined in claim 2 or claim 5, wherein said recurrence formula for said cortical bone density relative to said acoustic impedance is given by the following formula.

$$\rho = \alpha Zb + \beta$$

$\rho$: density of cortical bone [kg/m$^3$]
Zb: acoustic impedance of cortical bone in subject [kg/m$^2$sec]
$\alpha$: regression coefficient [sec/m]
$\beta$: section [kg/m$^3$]

13. An apparatus for diagnosing osteoporosis as defined in claim 12, wherein said regression coefficient $\alpha$ is established within the range of $1.27 \times 10^{-4}$ to $2.34 \times 10^{-4}$.

14. An apparatus for diagnosing osteoporosis as defined in claim 12, wherein said section $\beta$ is established within the range of 646 to 887.

15. An apparatus for diagnosing osteoporosis as defined in claim 2 or claim 5, wherein said recurrence formula for cortical bone density relative to acoustic impedance is given by the following formula.

$$\rho = BZb^A$$

$\rho$: density of cortical bone [kg/m$^3$]

Zb: acoustic impedance of cortical bone in subject [kg/m$^2$sec]

A: regression coefficient

B: constant [sec/m]

16. An apparatus for diagnosing osteoporosis as defined in claim 15, wherein said regression coefficient A is established within the range of 0.239 to 0.445.

17. An apparatus for diagnosing osteoporosis as defined in claim 15, wherein said constant B is established within the range of $10^{0.239}$ to $10^{1.55}$.

18. An ultrasonic reflection type of apparatus for diagnosing osteoporosis having an ultrasonic transducer for transmitting and receiving ultrasonic pulses, wherein the ultrasonic pulses are repeatedly radiated toward cortical bone in a subject, the echoes reflected on the surface of the cortical bone at that time are received, complex acoustic characteristics data of the subject's cortical bone are calculated based on the resulting echo data, and osteoporosis is diagnosed based on complex acoustic characteristics data thus calculated, said apparatus for diagnosing osteoporosis comprising:

echo waveform detecting means for detecting the reception waveform of the echoes reflected on the surface of the cortical bone when the ultrasonic pulses are radiated;

maximum echo waveform extracting means for extracting the maximum echo reception waveform by comparing the plurality of the echo reception waveforms thus detected;

Fourier transform treatment means for finding the maximum echo spectrum by the Fourier transform treatment of the maximum echo reception waveform; and complex reflection coefficient calculating means for calculating the ultrasonic complex reflection coefficient of cortical bone relative to the soft tissue of the subject based on the maximum echo spectrum thus determined.

19. An apparatus for diagnosing osteoporosis as defined in claim 18, further comprising a diagnostic means for diagnosing osteoporosis based on the amplitude data and phase data obtained from ultrasonic complex reflection coefficient thus calculated.

20. An ultrasonic reflection type of apparatus for diagnosing osteoporosis having an ultrasonic transducer for transmitting and receiving ultrasonic pulses, wherein the ultrasonic pulses are repeatedly radiated toward cortical bone in a subject, the echoes reflected on the surface of the cortical bone at that time are received, complex acoustic characteristics data of the subject's cortical bone are calculated based on the resulting echo data, and osteoporosis is diagnosed based on complex acoustic characteristics data thus calculated, said apparatus for diagnosing osteoporosis comprising:

echo waveform detecting means for detecting the reception waveform of the echoes reflected on the surface of the cortical bone when the ultrasonic pulses are radiated;

maximum echo waveform extracting means for extracting the maximum echo reception waveform by comparing the plurality of the echo reception waveforms thus detected;

Fourier transform treatment means for finding the maximum echo spectrum by the Fourier transform treatment of the maximum echo reception waveform; and complex acoustic impedance calculating means for calculating the complex acoustic impedance of the subject's cortical bone based on the maximum echo spectrum thus determined.

21. An apparatus for diagnosing osteoporosis as defined in claim 20, wherein said complex acoustic impedance calculating means calculates the ultrasonic complex reflection coefficient of the cortical bone relative to the soft tissue of the subject based on the maximum echo spectrum determined by the Fourier transform treatment means, and then calculates the complex acoustic impedance of the subject's cortical bone based on ultrasonic complex reflection coefficient thus calculated.

22. An apparatus for diagnosing osteoporosis as defined in claim 21, wherein said acoustic impedance of the subject's cortical bone is given by the following formula, $$Zb(\omega) = Za(\omega)(R(\omega)+1)/(1-R(\omega))$$

$Zb(\omega)$: acoustic impedance of cortical bone in Subject during angular frequency $\omega$ $Za(\omega)$: acoustic impedance of soft tissue or acoustic impedance of water during angular frequency $\omega$ $R(\omega)$: ultrasonic complex reflection coefficient at interface between soft tissue and cortical bone of subject 23. An apparatus for diagnosing osteoporosis as defined in claim 20, 21, or 22, further comprising diagnostic means for diagnosing osteoporosis based on the amplitude data and phase data obtained from complex acoustic impedance thus calculated.

24. An ultrasonic reflection type of apparatus for diagnosing osteoporosis having an ultrasonic transducer for transmitting and receiving ultrasonic pulses, wherein the ultrasonic pulses are repeatedly radiated toward cortical bone in a subject, the echoes reflected on the surface of the cortical bone at that time are received, complex acoustic characteristics data of the subject's cortical bone are calculated based on the resulting echo data, and osteoporosis is diagnosed based on complex acoustic characteristics data thus calculated, said apparatus for diagnosing osteoporosis comprising:

an echo waveform detecting program containing a processing procedure for detecting the reception waveform of the echoes reflected on the surface of the cortical bone when the ultrasonic pulses are radiated;

a maximum echo waveform extracting program containing a processing procedure for extracting the maximum echo reception waveform by comparing the plurality of the echo reception waveforms thus detected;

a Fourier transform treatment program containing a processing procedure for finding the maximum echo spectrum by the Fourier transform treatment of the maximum echo reception waveform;

a complex reflection coefficient calculating program containing a processing procedure for calculating the ultrasonic complex reflection coefficient of cortical bone in the subject based on the maximum echo spectrum thus determined;

a first memory for storing various processing programs, including the echo waveform detecting program, maximum echo waveform extracting program, Fourier transform treatment program, and complex reflection coefficient calculating program;

a second memory for temporarily storing data, including the detected echo reception waveform, and the extracted maximum echo reception waveform and spectrum; and a central processing unit for calculating the ultrasonic complex reflection coefficient of the subjects' cortical bone by using said second memory to execute the various programs stored in said first memory.

25. An ultrasonic reflection type of apparatus for diagnosing osteoporosis having an ultrasonic transducer for transmitting and receiving ultrasonic pulses, wherein the ultrasonic pulses are repeatedly radiated toward cortical bone in a subject, the echoes reflected on the surface of the cortical bone at that time are received, complex acoustic characteristics data of the subject's cortical bone are calculated based on the resulting echo data, and osteoporosis is diagnosed based on complex acoustic characteristics data thus calculated, said apparatus for diagnosing osteoporosis comprising:

an echo waveform detecting program containing a processing procedure for detecting the reception waveform of the echoes reflected on the surface of the cortical bone when the ultrasonic pulses are radiated;

a maximum echo waveform extracting program containing a processing procedure for extracting the maximum echo reception waveform by comparing the plurality of the echo reception thus detected;

a Fourier transform treatment program containing a processing procedure for finding the maximum echo spectrum by the Fourier transform treatment of the maximum echo reception waveform;

a complex acoustic impedance calculating program containing a processing procedure for calculating the complex acoustic impedance of cortical bone in the subject based on the maximum echo spectrum thus determined;

a first memory for storing various processing programs, including the echo waveform detecting program, maximum echo waveform extracting program, Fourier transform treatment program, and complex acoustic impedance calculating program;

a second memory for temporarily storing data, including the detected echo reception waveform, and the extracted maximum echo reception waveform and spectrum; and a central processing unit for calculating the complex acoustic impedance of the subjects' cortical bone by using said second memory to execute the various programs stored in said first memory.

26. An apparatus for diagnosing osteoporosis as defined in claim 25, wherein said complex acoustic impedance calculating program contains the processing procedure for calculating the ultrasonic complex reflection coefficient of the cortical bone in the subject based on the maximum echo spectrum which has been determined, and the processing procedure for calculating the acoustic impedance of the subject's cortical bone based on ultrasonic reflection coefficient thus calculated.

27. A method for diagnosing osteoporosis comprising the steps of:

setting an ultrasonic transducer on a predetermined area on the surface of a subject's skin;

repeatedly radiating ultrasonic pulses toward cortical bone below the skin;

receiving the echoes reflected on the surface of the cortical bone at that time, so as to detect the echo level;

extracting the maximum echo level from the echo levels thus detected;

calculating the ultrasonic reflection coefficient at the interface between the soft tissue and the cortical bone of the subject based on maximum echo level thus calculated; and calculating the density of the subject's cortical bone using a predetermined recurrence formula for the cortical bone density relative to the ultrasonic reflection coefficient.

28. A method for diagnosing osteoporosis comprising the steps of:

setting an ultrasonic transducer on a predetermined area on the surface of a subject's skin;

repeatedly radiating ultrasonic pulses toward cortical bone below the skin;

receiving the echoes reflected on the surface of the cortical bone at that time, so as to detect the echo level;

extracting the maximum echo level from the echo levels thus detected;

calculating the acoustic impedance of the cortical bone of the subject based on the maximum echo level that has been extracted; and calculating the density of the subject's cortical bone using a predetermined recurrence formula for said cortical bone density relative to said acoustic impedance.

29. A method for diagnosing osteoporosis, comprising the steps of:

setting an ultrasonic transducer on a predetermined area on the surface of a subject's skin;

repeatedly radiating ultrasonic pulses toward cortical bone below the skin;

reflecting at the transducer surface the echoes reflected on the surface of the cortical bone at that time, so as to detect the echo level;

extracting the maximum echo level from the echo levels thus detected;

calculating the ultrasonic reflection coefficient at the interface between the soft tissue and the cortical bone of the subject, based on the maximum echo level that has been extracted;

calculating the acoustic impedance of the cortical bone of the subject based on ultrasonic reflection coefficient thus calculated; and calculating the density of the subject's cortical bone using a predetermined recurrence formula for said cortical bone density relative to said acoustic impedance.

30. A method for diagnosing osteoporosis as defined in claim 27, wherein said recurrence formula for said cortical bone density relative to said ultrasonic reflection coefficient is given in the form of the following formula.

$$\rho = \alpha' R + \beta'$$

$\rho$: density of cortical bone [kg/m$^3$]
R: ultrasonic reflection coefficient at interface between soft tissue and cortical bone of subject
$\alpha'$: regression coefficient [kg/m$^3$]
$\beta'$: section [kg/m$^3$]

31. A method for diagnosing osteoporosis as defined in claim 30, wherein said regression coefficient $\alpha'$ is established within the range of 588 to 1100.

32. A method for diagnosing osteoporosis as defined in claim 30, wherein said section $\beta'$ is established within the range of 953 to 1060.

33. A method for diagnosing osteoporosis as defined in claim 28 or claim 29, wherein said recurrence formula for said cortical bone density relative to said ultrasonic reflection coefficient is given in the form of the following formula.

$$\rho = B'R^{A'}$$

ρ: density of cortical bone [kg/m³]
R: ultrasonic reflection coefficient at interface between soft tissue and cortical bone of subject
A': regression coefficient
B': constant [sec/m]

34. A method for diagnosing osteoporosis as defined in claim 29, wherein said acoustic impedance of the subject's cortical bone is given by the following formula, $$Zb = Za(R+1)/(1-R)$$

Zb: acoustic impedance of cortical bone in subject
Za: acoustic impedance of soft tissue or acoustic impedance of water
R: ultrasonic reflection coefficient at interface between soft tissue and cortical bone of subject 35. A method for diagnosing osteoporosis as defined in claim 28 or claim 29, wherein said recurrence formula for cortical bone density relative to acoustic impedance is given by the following formula.

$$\rho = \alpha Zb + \beta$$

ρ: density of cortical bone [kg/m³]
Zb: acoustic impedance of cortical bone in subject [kg/m²sec]
α: regression coefficient [sec/m]
β: section [kg/m³]

36. A method for diagnosing osteoporosis as defined in claim 35, wherein said regression coefficient α is established within the range of $1.27 \times 10^{-4}$ to $2.34 \times 10^{-4}$.

37. A method for diagnosing osteoporosis as defined in claim 35, wherein said section β is established within the range of 646 to 887.

38. A method for diagnosing osteoporosis as defined in claim 28 or claim 29, wherein said recurrence formula for cortical bone density relative to acoustic impedance is given by the following formula.

$$\rho = BZb^{A}$$

ρ: density of cortical bone [kg/m³]
Zb: acoustic impedance of cortical bone in subject [kg/m²sec]
A: regression coefficient
B: constant [sec/m]

39. A method for diagnosing osteoporosis as defined in claim 38, wherein said regression coefficient A is established within the range of 0.239 to 0.445.

40. A method for diagnosing osteoporosis as defined in claim 38, wherein said constant B is established within the range of $10^{0.239}$ to $10^{1.55}$.

41. A method for diagnosing osteoporosis, comprising the steps of:

setting an ultrasonic transducer a predetermined area on the surface of a subject's skin;
repeatedly radiating ultrasonic pulses toward cortical bone below the skin;
receiving the reception waveform of the echoes reflected on the surface of the cortical bone at that time, so as to detect the echo reception waveform;
extracting the detected maximum echo from the echo reception waveform;
determining the maximum echo spectrum by the Fourier transform treatment of the maximum echo reception waveform;
calculating the ultrasonic complex reflection coefficient of the cortical bone relative to the soft tissue of the subject based on the maximum echo spectrum that has been determined; and
diagnosing osteoporosis based on the amplitude data and phase data obtained from ultrasonic complex reflection coefficient thus calculated.

42. A method for diagnosing osteoporosis, comprising the steps of:

setting an ultrasonic transducer on a predetermined area on the surface of a subject's skin;
repeatedly radiating ultrasonic pulses toward cortical bone below the skin;
receiving the reception waveform of the echoes reflected on the surface of the cortical bone at that time, so as to detect the echo reception waveform;
extracting the maximum echo from the detected echo reception waveform;
determining the maximum echo spectrum by the Fourier transform treatment of the maximum echo reception waveform;
calculating the complex acoustic impedance of the cortical bone of the subject based on the maximum echo spectrum that has been determined; and
diagnosing osteoporosis based on the amplitude data and phase data obtained from complex acoustic impedance thus calculated.

43. A method for diagnosing osteoporosis, comprising the steps of:

setting an ultrasonic transducer on a predetermined area on the surface of a subject's skin;
repeatedly radiating ultrasonic pulses toward cortical bone below the skin;
receiving the reception waveform of the echoes reflected on the surface of the cortical bone at that time, so as to detect the echo reception waveform;
extracting the maximum echo from the echo reception waveform thus detected;
determining the maximum echo spectrum by the Fourier transform treatment of the maximum echo reception waveform;
calculating the ultrasonic complex reflection coefficient of the cortical bone relative to the soft tissue of the subject based on the maximum echo spectrum that has been determined;
calculating the complex acoustic impedance of the cortical bone of the subject based on ultrasonic complex reflection coefficient thus calculated; and diagnosing osteoporosis based on the amplitude data and phase data obtained from complex acoustic impedance thus calculated.

44. A method for diagnosing osteoporosis as defined in claim 43, wherein said acoustic impedance of the subject's cortical bone is given by the following formula.

$$Zb(\omega)=Za(\omega)(R(\omega)+1)/(1-R(\omega))$$

$Zb(\omega)$: acoustic impedance of cortical bone in Subject during angular frequency $\omega$ $Za(\omega)$: acoustic impedance of soft tissue or Acoustic impedance of water during angular frequency $\omega$ $R(\omega)$: ultrasonic complex reflection coefficient at interface between soft tissue and cortical bone of subject.

45. A method for diagnosing osteoporosis as defined in any one of claim 27 through claim 44, wherein the cortical bone which is the subject of diagnosis is the cortical bone of the cranial bone, tibia, or scapula.

* * * * *